United States Patent
Narr et al.

[11] 3,975,384
[45] Aug. 17, 1976

[54] 2,4,5,6-TETRASUBSTITUTED PYRIMIDINES AND SALTS THEREOF

[75] Inventors: Berthold Narr; Josef Roch; Erich Müller; Walter Haarmann, all of Biberach, an der Riss, Germany

[73] Assignee: Boehringer Ingelheim GmbH, Ingelheim am Rhein, Germany

[22] Filed: Aug. 14, 1974

[21] Appl. No.: 497,459

[30] Foreign Application Priority Data
Aug. 20, 1973 Germany............................ 2341925
June 26, 1974 Germany............................ 2430644

[52] U.S. Cl. .................. 260/243 R; 260/243 B; 260/247.1 M; 260/247.2 B; 260/247.5 D; 260/251 R; 260/253; 260/256.4 C; 270/256.4 N; 260/256.5 R; 424/246; 424/248; 424/251; 424/253

[51] Int. Cl.²...................................... C07D 417/14

[58] Field of Search...... 260/243 R, 247.1, 247.2 A, 260/253, 243 B, 256.4 N, 256.4 C, 247.5 D, 246 B, 247.1 M, 247.2 R, 247.2 B

[56] References Cited
UNITED STATES PATENTS

| | | | |
|---|---|---|---|
| 3,635,962 | 1/1972 | Wyss | 260/243 B |
| 3,835,132 | 9/1974 | Carr et al. | 260/247.5 D |
| 3,856,772 | 12/1974 | Dunkelmann et al. | 260/154 |

FOREIGN PATENTS OR APPLICATIONS
13,751    1965    Japan

*Primary Examiner*—R. Gallagher
*Attorney, Agent, or Firm*—Hammond & Littell

[57] ABSTRACT

Compounds of the formula

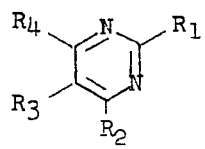

wherein
R₁ is alkoxy of 1 to 3 carbon atoms, morpholino, thiomorpholino, 1-oxido-thiomorpholino, 1,1-dioxido-thiomorpholino, or

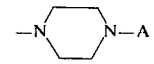

where
A is hydrogen, alkanoyl of 1 to 4 carbon atoms, alkenoyl of 2 to 4 carbon atoms, methoxy-(alkanoyl of 1 to 4 carbon atoms), carboxyl-(alkanoyl of 1 to 4 carbon atoms), acetyl-(alkanoyl of 1 to 4 carbon atoms), methoxy-(alkenoyl of 2 to 4 carbon atoms), carboxyl-(alkenoyl of 2 to 4 carbon atoms), acetyl-(alkenoyl of 2 to 4 carbon atoms), aminocarbonyl, mono(alkyl of 1 to 4 carbon atoms)-aminocarbonyl, di-(alkyl of 1 to 4 carbon atoms)-aminocarbonyl, methoxymethylaminocarbonyl, pyridinoyl, salicyloyl, furanoyl, or (alkyl of 1 to 3 carbon atoms)-sulfonyl, R₂ is morpholino, thiomorpholino, 1-oxido-thiomorpholino, 1,1-dioxido-thiomorpholino, piperazino or N′-[acetyl-(alkanoyl of 1 to 3 arbon atoms)]-piperazino, R₃ is hydrogen, chlorine, bromine, nitro, cyano, formyl, acetyl or carbalkoxy of 2 to 4 carbon atoms, and R₄ is hydrogen, chlorine, bromine, cyano, carbalkoxy of 2 to 4 carbon atoms, alkyl of 1 to 6 carbon atoms, mono(carbalkoxy of 2 to 4 carbon atoms)-alkyl of 1 to 6 carbon atoms, di(carbalkoxy of 2 to 4 carbon atoms)-alkyl of 1 to 6 carbon atoms, hydroxyl, allyloxy, alkoxy of 1 to 6 carbon atoms, mercapto, allylmercapto, (alkyl of 1 to 6 carbon atoms)-mercapto, 1-oxidothiomorpholino, or

—NHB where
B is hydrogen, alkyl of 1 to 3 carbon atoms, cyclohexyl, phenyl, chloro-phenyl, carboxy-phenyl, carbomethoxy-phenyl or pyridyl, and non-toxic, pharmacologically acceptable acid addition salts thereof; the compounds as well as the salts are useful as antithrombotics.

9 Claims, No Drawings

2,4,5,6-TETRASUBSTITUTED PYRIMIDINES AND SALTS THEREOF

This invention relates to a novel class of tetrasubstituted pyrimidines and non-toxic acid addition salts, as well as to a method of preparing these compounds.

More particularly, the present invention relates to a novel genus of substituted pyrimidine represented by the formula

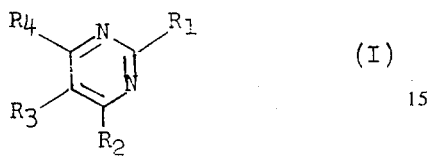

(I)

wherein

R$_1$ is alkoxy of 1 to 3 carbon atoms, morpholino, thiomorpholino, 1-oxido-thiomorpholino, 1,1-dioxide-thiomorpholino, or

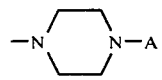

where
A is hydrogen, alkanoyl or 1 to 4 carbon atoms, alkenoyl of 2 to 4 carbon atoms, methoxy-(alkanoyl of 1 to 4 carbon atoms), carboyxl-(alkanoyl of 1 to 4 carbon atoms), acetyl-(alkanoyl of 1 to 4 carbon atoms), methoxy-(alkenoyl of 2 to 4 carbon atoms), carboxyl-(alkenoyl of 2 to 4 carbon atoms), acetyl-(alkenoyl of 2 to 4 carbon atoms), aminocarbonyl, mono(alkyl of 1 to 4 carbon atoms)-aminocarbonyl, di-(alkyl of 1 to 4 carbon atoms)-aminocarbonyl, methoxymethyl-aminocarbonyl, pyridinoyl, salicyloyl, furanoyl, or (alkyl of 1 to 3 carbon atoms) -sulfonyl R$_2$ is morpholino, thiomorpholino, 1-oxido-thiomorpholino, 1,1-dioxido-thiomorpholino, piperazino or N'-[acetyl-(alkanoyl of 1 to 3 carbon atoms)]-piperazino, R$_3$ is hydrogen, chlorine, bromine, nitro, cyano, fromyl, acetyl or carbalkoxy of 2 to 4 carbon atoms, and R$_4$ is hydrogen, chlorine, bromine, cyano, carbalkoxy of 2 to 4 carbon atoms, alkyl of 1 to 6 carbon atoms, mono(carbalkoxy of 2 to 4 carbon atoms)-alkyl of 1 to 6 carbon atoms, di(carbalkoxy of 2 to 4 carbon atoms)-alkyl of 1 to 6 carbon atoms, hydroxyl, allyloxy, alkoxy of 1 to 6 carbon atoms, mercapto, allylmercapto, (alkyl of 1 to 6 carbon atoms)-mercapto 1-oxido-thiomorpholino, or

—NHB where
B is hydrogen, alkyl of 1 to 3 carbon atoms, cyclohexyl, phenyl, choro-phenyl, carboxy -phenyl, carbomethoxy-phenyl or pyridyl, and non-toxic, pharmacologically acceptable acid addition salts thereof.

A sugbenus thereunder is constituted by compounds of the forumla

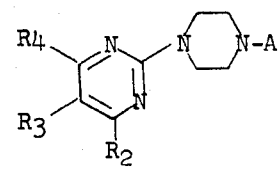

(Ia)

wherein
A is hydrogen, alkanoyl of 1 to 4 carbon atoms or acetyl-(alkanoyl of 1 to 4 carbon atoms), R$_2$ is thiomorpholino, 1-oxido-thiomorpholino or 1,1-dioxido-thiomorpholino, R$_3$ is chlorine, bromine or nitro, and R$_4$ is cyano, alkyl of 1 to 3 carbon atoms, alkoxy of 1 to 6 carbon atoms or (alkyl of 1 to 6 carbon atoms)-mercapto, and non-toxic, pharmacologically acceptable acid addition salts thereof.

The compounds embraced by formula I are prepared by reacting a compound of the formula

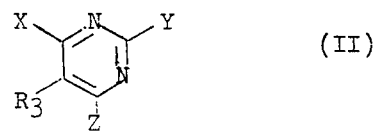

(II)

wherein
R$_3$ has the same meanings as in formula I, one or two of substituents X, Y and Z are so-called leaving-groups, and the remaining one or two of substituents X, Y and Z already have the meanings defined for R$_4$, R$_1$ and R$_2$, respectively, in connection with formula I, with a compound of the formula

H — D (III)

wherein D has the meanings defined for R$_1$, R$_2$ or R$_4$ in formula I.

Preferred embodiments of the leaving-groups above referred to are halogen, such as chlorine or bromine, hydroxyl, mercapto or sulfonyl; or substituted hydroxyl, mercapto, sulfinyl or sulfonyl radicals, such as methoxy, ethoxy, phenoxy, methylthio, benzylthio, methylsulfinyl, methylsulfonyl or ethylsulfonyl.

Depending upon the reactivity of the exchangeable or leaving-group substituent in formula II, the reaction is carried out at a temperature between −20° and +250°C, optionally in the presence of an acid-binding agent, and advantageously in a solvent medium, such as dioxane, acetone, glycol dimethyl ether, dimethylformamide, dimethylsulfoxide, ethanol or an excess over the stoichiometrically required amount of an amine of the formula III. However, the reaction may also be performed without a solvent.

For the preparation of a compound of the formula I, wherein R$_1$ and/or R$_2$ is N'-unsubstituted piperazino, it may further be of advantage if the imino group in a compound of the formula II and/or an imino group in a correspondingly substituted amine of the formula III is protected by a conventional protective group, for instance by an acyl group, such as carbethoxy, formyl, acetyl or benzoyl. This protective group may subsequently be split off again, for example by hydrolysis in the presence of an acid or a base and at temperatures up to the boiling point of the solvent which is used. The removal of a protective acyl group form an S-oxide compound is, however, preferably carried out by hydrolysis in the presence of a base, such as potassium hydroxide.

In those cases where the above-described method yields a compound of the formula I which contains a thiomorpholino group, this compound may be converted into the corresponding S-oxide compound or S, S-dioxide compound by oxidation; or if a compound of the formula I is obtained wherein the N'-position of the piperazino radical is substituted by an acyl or aminocarbonyl group, this compound may be converted into the corresponding N'-unsubstituted piperazino compound of the formula I by hydrolysis; or if a compound of the formula I containing a free imino group is obtained, this compound may be converted into the corresponding acylated compound of the formula I by acylation or carbamoylation; or if a compound of the formula I is obtained wherein $R_3$ is hydrogen, this compound may be converted into the corresponding 5-nitro compound of the formula I by nitration.

The subsequent oxidation of a thiomorpholino group is effected with a conventional oxidizing agent, such as hydrogen peroxide, peracetic acid, sodium metaperiodate or potassoium permanagate, preferably in the presence of a solvent, such as glacial acetic acid, and preferably at temperatures between 0° and 80°C. If the oxidation is, for example, effected with hydrogen peroxide, peracetic acid or sodium metaperiodate, the corresponding 1-oxido-thiomorpholino compound of the formula I is obtained, but if the oxidation is performed with potassium permanganate, the corresponding 1,1-dioxidothiomorpholino compound of the formula I is obtained.

The subsequent hydrolysis for removal of an N'-substituent on a piperazino group is performed in the presence of a base, such as sodium hydroxide or potassium hydroxide, or of an aicd, such as hydrochloric acid, preferably in the presence of a solvent such as water, ethanol, isopropanol or water/ethanol, and preferably at the boiling point of the solvent which is used, for instance at temperatures between 80° and 100°C.

The subsequent acylation of an N'-unsubstituted piperazino group is preferably performed with a corresponding carboxylic acid in the presence of a dehydrating agent, such an N,N-dicyclohexyl-carbodiimide or thionylchloride, or with a reactive derivative of the corresponding carboxylic acid, such as a halide, anhydride, ester or mixed anhydride thereof, optionally in the presence of a base, such as sodium carbonate, triethylamine or pyridine, and advantageously in the presence of a solvent, such as ether, dioxane, benzene or pyridine, preferably at temperatures between 0° and 100°C.

The subsequent nitration of a 5-unsubstituted pryimidine is carried out with a nitrating agent, such as sulfuric acid/nitric acid or nitric acid by itself at elevated temperatures, for example at temperatures between 50° and 80°C.

Some of the starting compounds of the formula II are described in the literature, and the others may be prepared by known processes (see Examples A–Z):

Thus a compound of the formula II with only one or two exchangeable groups is obtained from a precursor in which more exchangeable groups are bonded to the pyrimidine nucleus, by reaction with a compound of the formula III. On the other hand, it is also possible to subsequently alter in a compound of the formula II those groups X, Y and/or Z which do not represent exchangeable groups, for example to subsequently oxidize a thiomorpholino-pyrimidine, to subsequently deacylate an N'-formyl-piperazino group, or to alkylate a thio group. Also, the exchange of an exchangeable group for a more reactive exchangeable group is another way to prepare the starting compounds of the formula II.

The compounds embraced by formula I are organic bases and therefore form acid addition salts with inorganic or organic acids. Examples of non-toxic, pharmacologically acceptable acid addition salts are those formed with hydrochloric acid, hydrobromic acid, sulfuric acid, phosphoric acid, fumaric acid, succinic acid, lactic acid, citric acid, tartaric acid, maleic acid, 8-chlorotheophylline or the like.

The following examples further illustrate the present invention and will enable others skilled in the art to understand it more completely. It should be understood, however, that the invention is not limited solely to the particular examples given below. Preparation of starting compounds of the formula II:

EXAMPLE A 2-(N'-carbethoxy-piperazino)-4-chloro-6-aminopyrimidine 29.0 gm of 2,4-dichloro-6-aminopyrimidine [H. Bretschneider et al, Monatsh. f. Chemie 92, 132 (1961)]were suspended in 150 ml of dioxane, the suspension was heated to 80°C, and 60.2 gm of N-carbethoxy-piperazine were added. After standing for 40 minutes at this temperature, the mixture was poured into 500 ml of water, and the aqueous solution was on an ice bath while stirring. The initially oily precipitating product crystallized after about 15 minutes. The crystals were suction-filtered off and recrystallized from 300 ml of methanol. Yield: 28.8 gm (57.3% of theory); m.p. 163°–166°C.

EXAMPLE B 2-(N'-carbethoxy-piperazino)-4,6-dichloro-pyrimidine 79.0 gm of 2-methylthio-barbituric acid [Koppel, Springer and Robins, J. Org. Chem. 26, 792 to 803 (1961)] were heated with 94 gm of carbethoxypiperazine in 100 ml of dimethyl formamide at 120°C for 3 hours, whereby methyl mercaptan escaped. Then, the mixture was cooled, diluted with water and stirred until crystals of 2-(N'-carbethoxy-piperazino)-4,6-dihydroxy-pyrimidine were obtained. Yield: 68.6 gm (51.4% of theory).

13.4 gm of the crude product thus obtained were refluxed for 1.5 hours with 92 ml of phosphorus oxychloride, and the reaction mixture was then evaporated to dryness. The residue was decomposed on ice. The precipitate was suction filtered, dried and refluxed for 4 hours in ethanol to convert the 2-(N'-chlorocarbonyl-piperazino)-4,6-dichloro-pyrimidine side product completely into 2-(N'-carbethoxy-piperazino)-4,6-dichloro-pyrimidine [monitored by thin-layer chromatography (silicagel plate; eluant: n-pentane/ethyl acetate = 7:3)].

After evaporation of the alcoholic solution, white crystals were obtained. Yield: 37.9 gm (49.9% of theory), m.p. 136°–143°C.

EXAMPLE C

4-Thiomorpholino-2,6-dichloro-pyrimidine 275 gm of 2,4,6-trichloro-pyrimidine were dissolved in 1.8 liters of acetone, and the solution was added slowly to a mixture of 250.3 gm of triethylamine and 170.5 gm of thiomorpholine in 0.7 liter of acetone, while stirring, so that the temperature did not rise above 40°C. Then, the mixture was stirred for 45 minutes more, whereby the temperature dropped to 30°C.

The precipitated triethylamine hydrochloride was suction-filtered off, washed with acetone and the filtrate was evaporated in a rotation evaporator. The evaporation residue was recrystallized from 2.3 liters of ethanol; 222.7 gm of white crystalline 2,6-dichloro-4-thiomorpholino-pyrimidine were obtained, which were again recrystallized from 2.2 liters of ethanol. A first fraction of 196.5 gm of pure white crystals was obtained, and 17.9 gm more precipitated from the evaporated mother liquor. Yield: 214.4 gm (57.1% of theory); m.p. 118°–121.5°C.

EXAMPLE D

2-Thiomorpholino-4,6-dichloro-pyrimidine

From the mother liquor of the first crystallization in Example C the isomeric 2-thiomorpholino-4,6-dichloro-pyrimidine also formed was obtained quantitatively by column chromatography of the evaporation residue (silicagel, grain size = 0.2 to 0.5 mm; eluant: toluene; ratio between substance layer and silicagel = 1:10). The first fractions contained all of the product. Yield: 79.0 gm (21.0% of theory), m.p. 79.5°–81.5°C.

EXAMPLE E

2-(N'-formyl-piperazino)-4-(1-oxido-thiomorpholino)-5-nitro-6-chloro-pyrimidine 100 gm of 2-(N'-formyl-piperazino)-4-thiomorpholino-6-chloro-pyrimidine (m.p. 195°–198°C) were added in small amounts to 570 ml of concentrated sulfuric acid while stirring; the temperature was held at about 20°C by cooling occasionally. To dissolve the substance completely, the mixture was stirred for about 30 to 40 minutes. After cooling to 0°C, 115 ml of fuming nitric acid were slowly added dropwise; the temperature was held at about 5°C by cooling. Afterwards, the mixture was stirred for 20 minutes more, and then the cold, yellow reaction solution was poured into about 3 liters of crushed ice. A greasy, yellow product precipitated. This product was extracted once with 1.2 liters of chloroform and then again twice with 0.7 liter of chloroform each, the combined extracts were dried over sodium sulfate and evaporated in a rotation evaporator. The yellow, resinous residue was taken up in 1.1 liters of hot ethanol, the solution was slowly cooled to 25° to 30°C, and seed crystals were added. The mixture was stirred for a further hour at room temperature and then cooled with ice water to complete the crystallization. After standing for 20 minutes at a temperature of about 5°C, the mixture was suction-filtered, and the filter cake was washed with cold ethanol and dried over sulfuric acid in a desiccator. Yield: 104 gm (87.74% of theory), m.p. 176°–178°C.

6-Ethoxy-5-nitro-4-(1-oxido-thiomorpholino)-2-piperazinopyrimidine was prepared in analogous manner from 6-ethoxy-2-piperazino-4-thiomorpholino-pyrimidine and concentrated sulfuric acid/concentrated nitric acid, except that before extracting with chloroform the mixture was adjusted to a pH-value of 9 by addition of sodium hydroxide solution. M.p. 223°–224°C (ethanol).

EXAMPLE F

2-Methylmercapto-4-thiomorpholino-5-nitro-6-cyclohexylaminopyrimidine 14.0 gm of 2-methylmercapto-4,6-dichloro-5-nitropyrimidine (Brown and Jacobsen, J. Chem. Soc. 1963, 3776) were dissolved in 200 ml of methanol, the solution was cooled to −60°C, and 6.0 gm of triethylamine were added. Over a period of 1 hour 4.0 gm of cyclohexylamine were added dropwise, while stirring, without exceeding the temperature of −60°C. Afterwards, the methanol was distilled off, the residue was taken up in chloroform, and the solution was washed 5 times with water. After distilling off the chloroform, the residue was recrystallized from isopropanol, and pure 2-methyl-mercapto-4-chloro-5-nitro-6-cyclohexylamino-pyrimidine was obtained. Yield: 11.2 gm (62% of theory), m.p. 98°–104°C.

3.0 gm of 2-methylmercapto-4-chloro-5-nitro-6-cyclohexylamino-pyrimidine were dissolved in 30 ml of acetone, a solution of 1.38 gm of potassium carbonate in 1.5 ml of water was added, and the mixture was admixed with a solution of 1.2 gm of thiomorpholine in 10 ml of acetone. The resulting mixture was stirred at room temperature, whereby after a short time a voluminous, crystalline precipitate was formed which was further increased by addition of water. The mixture was suction-filtered and the filter cake, 2-methylmercapto-4-thiomorpholino-5-nitro-6-cyclohexylamino-pyrimidine, was recrystallized from isopropanol. Yield: 2.3 gm (62% of theory), m.p. 145°–146°C.

EXAMPLE G

2-(1-Oxido-thiomorpholino)-4-(N'-formyl-piperazino)-5-nitro-6-chloro-pyrimidine was prepared analogous to Example E from 2-thiomorpholino-4-(N'-formyl-piperazino)-6-chloro-pyrimidine with a mixture of fuming nitric acid and concentrated sulfuric acid. Yield: 89.4% of theory, m.p. 129°–133°C.

EXAMPLE H

2-Thiomorpholino-4-chloro-pyrimidine and 4-Thiomorpholino-2-chloro-pyrimidine A solution of 8.0 gm (0.054 mol) of 2,4-dichloropyrimidine in 1330 ml of acetone was admixed dropwise at −35°C, while stirring, with a solution of 6.1 gm (0.059 mol) of thiomorpholine in 15 ml of water and with a solution of 8.1 gm (0.059 mol) of potassium carbonate in 15 ml of water. The mixture was stirred for 2.5 hours more at room temperature, the acetone was evaporated in vacuo, and the residue was taken up in water, dried and purified by chromatography on 250 gm of silicagel (activity stage I, grain size 0.05 to 0.2 mm) with benzene/ethyl acetate = 5:1.

The substance with a high $R_f$-value was 2-thiomorpholino-4-chloro-pyrimidine, m.p. 64°–65°C (from isopropanol), yield: 0.7 gm (6% of theory).

The substance with a lower $R_f$-value was 4-thiomorpholino-2-chloro-pyrimidine of m.p. 106°–108°C (from isopropanol), yield: 8.9 gm (77% of theory).

The following isomeric compounds were prepared in analogous manner:

a. 5-Cyano-2,6-dichloro-4-thiomorpholino-pyrimidine (m.p. 180°C, yield: 41.7% of theory) and 5-Cyano-4,6-dichloro-2-thiomorpholino-pyrimidine (m.p. 99°C, yield: 4.5% of theory)
from 5-cyano-2,4,6-trichloro-pyrimidine and thiomorpholine.

b. 5-Cyano-2,4-dichloro-6-methoxy-pyrimidine (m.p. 117°C, yield: 20.4% of theory) and 5-Cyano-4,6-dichloro-2-methoxy-pyrimidine (m.p. 156°C, yield: 10% of theory)
from 5-cyano-2,4,6-trichloro-pyrimidine and methanol (reaction time: 20 hours; reaction temperature: 65°C; without potassium carbonate).

EXAMPLE I

6-Ethoxy-4-chloro-2-methylthio-5-nitro-pyrimidine 24 gm (0.1 mol) of 4,6-dichloro-2-methylthio-5-nitro-pyrimidine (prepared analogous to Brown and Jacobsen, J. Chem. Soc. 1965, 3776) were suspended at 0°C in 200 ml of ethanol. Over a period of 20 minutes a sodium ethylate solution, prepared from 2.35 gm (0.102 gram-atom) of sodium and 80 ml of ethanol, was added dropwise to the suspension, while stirring, and afterwards the mixture was stirred for 45 minutes more at 0°C.

The reaction mixture was then poured over 700 gm of crushed ice, and the precipitated yellow crystals were suction-filtered off, dried and recrystallized from petroleum ether (b.p. 60°–100°C). Yield: 20.8 gm (83.5% of theory); m.p. 83°–85.5°C.

In analogous manner the following compounds were prepared by reaction of 4,6-dichloro-2-methylthio-5-nitropyrimidine and the corresponding sodium alcoholate:

a. 4-Chloro-6-methoxy-2-methylthio-5-nitro-pyrimidine, m.p. 77.5°–79.5°C (petroleum ether);

b. 4-Chloro-2-methylthio-5-nitro-6-n-propoxy-pyrimidine, an oil, $R_f$-value = 0.4; silicagel, benzene/petroleum ether = 1:1;

c. 4-Chloro-6-isopropoxy-2-methylthio-5-nitro-pyrimidine, m.p. 55°–57°C (petroleum ether);

d. 6-Allyloxy-4-chloro-2-methylthio-5-nitro-pyrimidine, m.p. 51°–52°C, b.p.: 145°–148°C at 0.2 mm Hg;

e. 6-n-Butoxy-4-chloro-2-methylthio-5-nitro-pyrimidine, an oil, $R_f$-value = 0.45; silicagel, benzene/petroleum ether = 1:1;

f. 6-sec. Butoxy-4-chloro-2-methylthio-5-nitro-pyrimidine, an oil, $R_f$-value = 0.45; silicagel, petroleum ether/ethyl acetate = 1:1;

g. 4-Chloro-2-methylthio-6-neopentyloxy-5-nitro-pyrimidine, b.p.: 98°–103°C at 0.01 mm Hg.

EXAMPLE J

6-Ethoxy-2-methylthio-4-(1-oxido-thiomorpholino)-5-nitropyrimidine 15 gm (0.06 mol) of 6-ethoxy-4-chloro-2-methylthio-5-nitro-pyrimidine were suspended, together with 5 gm of potassium carbonate, in 150 ml of ethanol, a solution of 7.8 gm (0.066 mol) of thiomorpholine-1-oxide in 100 ml of ethanol was added, and the mixture was refluxed for 4 hours at 60°C. The reaction mixture was then poured into ice water. The yellow crystals formed thereby were suction-filtered off, dried and recrystallized from ethyl acetate in the presence of charcoal. Yield: 17.7 gm (88.5% of theory), m.p. 160°–162°C. In analogous manner the following compounds were prepared:

a. 6-Ethoxy-2-methylthio-4-thiomorpholino-5-nitro-pyrimidine from 6-ethoxy-4-chloro-2-methylthio-5-nitro-pyrimidine and thiomorpholine. M.p. 117.5°–119.5°C (ethyl acetate/petroleum ether).

b. 6-Ethoxy-2-methylthio-5-nitro-4-(1,1-dioxido-thiomorpholino)-pyrimidine from 6-ethoxy-4-chloro-2-methylthio-5-nitro-pyrimidine and thiomorpholine-1,1-dioxide. M.p. 160°–163°C (ethyl acetate).

c. 6-Ethoxy-2-methylthio-4-morpholino-5-nitro-pyrimidine from 6-ethoxy-4-chloro-2-methylthio-5-nitro-pyrimidine and morpholine; m.p. 114.5°–116°C (ethanol).

d. 6-Methoxy-2-methylthio-5-nitro-4-(1-oxido-thiomorpholino)-pyrimidine from 4-chloro-6-methoxy-2-methylthio-5-nitro-pyrimidine and thiomorpholine-1-oxide (reaction temperature 20°C, reaction time 15 hours); m.p. 175°–177.5°C (ethanol).

e. 6-Allyloxy-2-methylthio-5-nitro-4-thiomorpholino-pyrimidine from 6-allyloxy-4-chloro-2-methylthio-5-nitro-pyrimidine and thiomorpholine. (Reaction temperature 20°C, reaction time 2 hours). M.p. 89°–90.5°C (petroleum ether, b.p. 60°–80°C)

f. 6-Allyloxy-4-(1,1-dioxido-thiomorpholino)-2-methylthio-5-nitro-pyrimidine from 6-allyloxy-4-chloro-2-methylthio-5-nitro-pyrimidine and thiomorpholine-1,1-dioxide. (Reaction temperature 20°C, reaction time 2 hours), m.p. 147°–149°C (petroleum ether b.p.: 60°–80°C/ethyl acetate = 2:3).

g. 4-(1,1-Dioxido-thiomorpholino)-2-methylthio-5-nitro-6-n-propoxy-pyrimidine from 4-chloro-2-methylthio-5-nitro-6-n-propoxy-pyrimidine and thiomorpholine-1,1-dioxide. M.p. 160°–162°C (isopropanol).

h. 2-Methylthio-5-nitro-4-(1-oxido-thiomorpholino)-6-n-propoxy-pyrimidine from 4-chloro-2-methylthio-5-nitro-6-n-propoxy-pyrimidine and thiomorpholino-1-oxide. M.p. 146°–148°C (isopropanol).

i. 2-Methylthio-5-nitro-6-n-propoxy-4-thiomorpholino-pyrimidine from 4-chloro-2-methylthio-5-nitro-6-n-propoxy-pyrimidine and thiomorpholine. M.p. 76°–78.5°C (ethanol).

j. 2-Methylthio-4-morpholino-5-nitro-6-n-propoxy-pyrimidine from 4-chloro-2-methylthio-5-nitro-6-n-propoxy-pyrimidine and morpholine. M.p. 89°–90°C (isopropanol).

k. 4-(1,1-Dioxido-thiomorpholino)-2-methylthio-5-nitro-6-isopropoxy-pyrimidine from 4-chloro-2-methylthio-5-nitro-6-isopropoxy-pyrimidine and thiomorpholine-1,1-dioxide. M.p. 168°–170°C (isopropanol).

l. 2-Methylthio-5-nitro-4-(1-oxido-thiomorpholino)-6-isopropoxy-pyrimidine from 4-chloro-2-methylthio-5-nitro-6-isopropoxy-pyrimidine and thiomorpholine-1-oxide. M.p. 127°–129°C (isopropanol).

m. 2-Methylthio-5-nitro-6-isopropoxy-4-thiomorpholino-pyrimidine from 4-chloro-2-methylthio-5-nitro-6-isopropoxy-pyrimidine and thiomorpholine. M.p. 97°–98.5°C (petroleum ether).

n. 2-Methylthio-4-morpholino-5-nitro-6-iospropoxy-pyrimidine from 4-chloro-2-methylthio-5-nitro-6-isopropoxy-pyrimidine and morpholine. M.p. 80°–81°C (petroleum ether).

o. 6-n-Butoxy-4-(1,1-dioxido-thiomorpholino)-2-methylthio-5-nitro-pyrimidine from 6-n-butoxy-4-chloro-2-methylthio-5-nitro-pyrimidine and thiomorpholine-1,1-dioxide. M.p. 128°–130°C (ethanol).

p. 6-n-Butoxy-2-methylthio-5-nitro-4-(1-oxido-thiomorpholino)-pyrimidine from 6-n-butoxy-4-chloro-2- methylthio-5-nitro-pyrimidine and thiomorpholine-1-oxide. M.p. 129°–130.5°C (ethanol).

q. 6-n-Butoxy-2-methylthio-5-nitro-4-thiomorpholino-pyrimidine from 6-n-butoxy-4-chloro-2-methylthio-5-nitro-pyrimidine and thiomorpholine. M.p. 107°–109.5°C (cyclohexane).

r. 6-n-Butoxy-2-methylthio-4-morpholino-5-nitro-pyrimidine from 6-n-butoxy-4-chloro-2-methylthio-5-nitro-pyrimidine and morpholine. M.p. 98°–100°C (cyclohexane).

s. 6-sec.Butoxy-4-(1,1-dioxido-thiomorpholino)-2-methylthio-5-nitro-pyrimidine from 6-sec.butoxy-4-chloro-2-methylthio-5-nitro-pyrimidine and thiomorpholine-1,1-dioxide. M.p. 162.5°–164.5°C (ethanol).

t. 6-sec.Butoxy-2-methylthio-5-nitro-4-(1-oxido-thiomorpholino)-pyrimidine from 6-sec.butoxy-4-chloro-2-methylthio-5-nitro-pyrimidine and thiomorpholine-1-oxide. M.p. 121.5°–123°C (ethanol)

u. 6-sec.Butoxy-2-methylthio-5-nitro-4-thiomorpholino-pyrimidine from 6-sec.butoxy-4-chloro-2-methylthio-5-nitro-pyrimidine and thiomorpholine. M.p. 87.5°–89.5°C (cyclohexane).

v. 2-Methylthio-6-neopentoxy-5-nitro-4-(1-oxido-thiomorpholino)-pyrimidine from 4-chloro-2-methylthio-6-neopentoxy-5-nitro-pyrimidine and thiomorpholine-1-oxide. M.p. 125°–127°C (diisopropyl ether).

w. 2-Methylthio-6-neopentoxy-5-nitro-4-thiomorpholinopyrimidine from 4-chloro-2-methylthio-6-neopentoxy-5-nitro-pyrimidine and thiomorpholine. M.p. 102°–104°C (ethanol).

EXAMPLE K

6-Chloro-2-methylthio-5-nitro-4-(1-oxido-thiomorpholino)pyrimidine 36 gm (0.15 mol) of 4,6-dichloro-2-methylthio-5-nitro-pyrimidine were dissolved in 100 ml of acetone. After cooling the solution to −50°C, 35.7 gm (0.3 mol) of thiomorpholine-1-oxide were added dropwise. After stirring for another hour, the reaction mixture was poured over ice, and the precipitate formed thereby was suction-filtered off, dried and recrystallized from ethyl acetate. Yield: 80.4% of theory; m.p. 160°–162°C.

In analogous manner the following compounds were also prepared:

a. 6-Chloro-2-methylthio-5-nitro-4-thiomorpholino-pyrimidine from 4,6-dichloro-2-methylthio-5-nitro-pyrimidine and thiomorpholine (reaction temperature −50°C; reaction time 80 minutes). M.p. 138°–140°C (petroleum ether:ethyl acetate = 2:3)

b. 4-Amino-6-chloro-2-methylthio-5-nitro-pyrimidine from 4,6-dichloro-2-methylthio-5-nitro-pyrimidine and concentrated ammonia. M.p. 176°–177.5°C (carbon tetrachloride).

EXAMPLE L

6-Amino-2-methylthio-5-nitro-4-(1-oxido-thiomorpholino)pyrimidine 3.08 gm (0.014 mol) of 4-chloro-6-amino-2-methylthio-5-nitro-pyrimidine were dissolved in 50 ml of acetone, and a solution of 3.2 gm (0.027 mol) of thiomorpholine-1-oxide in 20 ml of acetone was added dropwise at room temperature, while stirring. After stirring the mixture for 1.5 hours more, ice was added to the reaction mixture, and the yellow precipitate formed thereby was suction-filtered off and recrystallized from ethanol. Yield: 78.2% of theory; m.p. 239°–242°C.

EXAMPLE M 2-(N′-Carbethoxy-piperazino)-4,6-dihydroxy-5-nitro-pyrimidine 100 gm (0.493 mol) of 2,4-dihydroxy-2-methylthio-5-nitro-pyrimidine (prepared analogous to Brown, Jacobsen J. Chem. Soc. 1965, 3776) were heated at 120°C for 30 minutes together with 156 gm (0.986 mol) of N-carbethoxy-piperazine. The reaction mixture, which solidified into a solid mass, was recrystallized from ethanol without further treatment. Yield: 140.5 gm (91.1% of theory); m.p. 220°–224°C.

4,6-Dihydroxy-5-nitro-2-thiomorpholino-pyrimidine was prepared in analogous manner from 4,6-dihydroxy-2-methylthio-5-nitro-pyrimidine and thiomorpholine. M.p. 220°–223°C.

EXAMPLE N 4,6-Dichloro-5-nitro-2-thiomorpholino-pyrimidine 190 gm (0.735 mol) of 2,4-dihydroxy-5-nitro-2-thiomorpholino-pyrimidine were added in small portions to a mixture of 1100 ml of phosphorus oxychloride and 190 ml of diethylaniline, whereby the temperature of the mixture rose to 60°C. The mixture was refluxed for 3 hours, 600 ml of phosphorus oxychloride were distilled off, and the residue was carefully poured over ice. The aqueous phase was extracted with chloroform, and the chloroform extract was dried over sodium sulfate, treated with charcoal and evaporated to dryness. The residue was recrystallized twice from benzene/petroleum ether. Yield: 44 gm (20.4% of theory); m.p. 164°–165°C.

2-(N′-Carbethoxy-piperazino)-4,6-dichloro-5-nitro-pyrimidine was prepared in analogous manner from 2-(N′-carbethoxy-piperazino)-4,6-dihydroxy-5-nitro-pyrimidine and phosphorus oxychloride. M.p. 120°–121.5°C (petroleum ether).

EXAMPLE O

6-Ethoxy-4-chloro-5-nitro-2-thiomorpholino-pyrimidine 14.8 gm (0.05 mol) of 4,6-dichloro-5-nitro-2-thiomorpholino-pyrimidine were dissolved in a mixture of 200 ml each of acetone and dioxane, and the solution was cooled to −20°C. A solution of sodium ethylate, prepared from 1.15 gm (0.05 mol) of sodium and 100 ml of ethanol, was added dropwise while stirring, at −20°C. The mixture was stirred another hour at room temperature, then poured over ice, and the product obtained thereby was recrystallized from isopropanol. Yield: 10.3 gm (67.5% of theory); m.p. 149°–150°C.

EXAMPLE P 2-(N′-Carbethoxy-piperazino)-6-chloro-4-thiomorpholinopyrimidine 7.0 gm (0.02 mol) of 2-(N′-carbethoxy-piperazino)-4,6-dichloro-5-nitro-pyrimidine were dissolved in 100 ml of acetone, the solution was cooled to −40°C, and first a solution of 5 gm of potassium carbonate in water was added and then a solution of 2.1 gm (0.02 mol) of thiomorpholine in 30 ml of acetone was added dropwise at −40°C while stirring. After stirring for 2 hours more at −40°C, the mixture was stirred again for 1.5 hours at room temperature. Then ice was added, and the precipitate formed thereby was suction-filtered off, dried and recrystallized from petroleum ether/ethyl acetate. Yield: 5.3 gm (64.7% of theory); m.p. 134.5°–136.5°C.

EXAMPLE Q

6-Ethoxy-2-piperazino-4-thiomorpholino-pyrimidine 9 gm (0.03 mol) of 6-chloro-2-(N'-formyl-piperazino)-4-thiomorpholino-pyrimidine (m.p. 198°–201°C) were added to a sodium ethylate solution prepared from 2.3 gm (0.1 mol) of sodium and 150 ml of ethanol, and the mixture was heated in an autoclave for 2 hours at 220°C. After cooling, the reaction mixture was poured into water, the aqueous mixture was extracted with chloroform, the chloroform phase was dried over sodium sulfate and evaporated to dryness. The residue was purified by column chromatography on silicagel (grain size 0.2 to 0.5 mm; eluant: chloroform/methanol = 9:1). The uniform fractions were combined and evaporated, yielding as a residue 6.8 gm (72.7% of theory) of the desired product.

EXAMPLE R

5-Carbamoyl-2,4,6-trihydroxy-pyrimidine

Prepared [see H. C. Scarborough, W. A. Gould, J. Org. Chem. 26, 3720 (1961)] from barbituric acid and urea (3 hours, 160°C). M.p. > 350°C; yield: 87.7% of theory.

5-Carbamoyl-4,6-di-hydroxy-2-thio-pyrimidine was prepared in analogous manner from thiobarbituric acid and urea (3 hours, 170°C). M.p. > 350°C.

EXAMPLE S

5-Carbamoyl-4,6-dihydroxy-2-methylthio-pyrimidine 5.6 gm (0.03 mol) of 5 carbamoyl-4,6-dihydroxy-2-thio-pyrimidine were added to a solution of 4.2 gm (0.105 mol) of sodium hydroxide in 150 ml of water, and 4.7 gm (0.033 mol) of methyl iodide were added at room temperature while stirring. After stirring for 3 hours more, the reaction mixture was acidified, and the precipitated product was suction-filtered off and recrystallized from dioxane. M.p. > 360°C, yield: 1 gm (16.6% of theory).

EXAMPLE T

5-Cyano-2,4,6-trichloro-pyrimidine

Prepared [see C.A. 62, 7775 (1965)] from 5-carbamoyl-2,4,6-trihydroxy-pyrimidine, phosphorus oxychloride and dimethyl aniline (18 hours, 100°C). M.p. 123°C (petroleum ether b.p.: 100°–140°C); yield: 65% of theory.

5-Cyano-4,6-dichloro-2-methylthio-pyrimidine was prepared in analogous manner from 5-carbamoyl-4,6-dihydroxy-2-methylthiopyrimidine and phosphorus oxychloride/diethyl aniline (4 hours, reflux). M.p. 107°C (petroleum ether).

EXAMPLE U 4,6-Dihydroxy-5-formyl-2-methylthio-pyrimidine was prepared from 4,6-dihydroxy-5-formyl-2-thio-pyrimidine in aqueous alkaline solution and methyl iodide by stirring for 4 hours at 0°C. Yield: 97.8% of theory; m.p. > 250°C.

EXAMPLE V 4,6-Dichloro-5-dichloromethyl-2-methylthio-pyrimidine 121 gm (0.58 mol) of 4,6-dihydroxy-5-formyl-2-methyl-thio-pyrimidine were carefully admixed with 600 ml of phosphorus oxychloride, whereby a vigorous reaction took place, and after it had subsided 80 ml of diethyl aniline were added. The mixture was refluxed for 6 hours, the excess phosphorus oxychloride was distilled off in vacuo, the residue was carefully admixed with ice, and the aqueous mixture was extracted with chloroform. The chloroform phase was washed, dried and evaporated to dryness in vacuo, and the residue was recrystallized from petroleum ether in the presence of charcoal. M.p. 66°C; yield: 70 gm (43.3% of theory).

EXAMPLE W

6-Ethoxy-5-formyl-2-methylthio-4-thiomorpholino-pyrimidine

A solution of 11.4 gm (0.041 mol) of 4,6-dichloro-5-dichloromethyl-2-methylthio-pyrimidine in 100 ml of ethanol was added dropwise, while stirring and cooling with ice, to a sodium ethylate solution prepared from 0.95 gm (0.041 mol) of sodium and 50 ml of ethanol. After stirring it for another hour, the reaction mixture was admixed with water and extracted with chloroform. After evaporating the chloroform, the residue was dissolved in dioxane, the solution was admixed with 31 gm (0.3 mol) of thiomorpholine while stirring and cooling, and the mixture was left standing overnight at 20°C. After diluting with water, the mixture was extracted with chloroform, the chloroform phase was washed and dried, and the chloroform was distilled off. The residue was purified by column chromatography on silicagel (grain size 0.2 to 0.5 mm; eluant: benzene/ethyl acetate = 5:1). The combined uniform fractions were evaporated to dryness, and the residue was recrystallized from petroleum ether. M.p. 101°C; yield: 5.6 gm (45.6% of theory).

Analysis: $C_{12}H_{17}N_3O_2S_2$; molecular weight 299.42 Calculated: C - 48.14%; H - 5.72%; N - 14.03%. Found: C - 48.45%; H - 5.82%; N - 13.78%.

6-Ethoxy-5-formyl-2-methylthio-4-(1-oxido-thiomorpholino)pyrimidine was prepared in analogous manner from 4,6-dichloro-5-dichloromethyl-2-methylthio-pyrimidine, sodium ethylate and thiomorpholine-1-oxide. M.p. 163°C (ethyl acetate/dioxane).

EXAMPLE X

5-Carbethoxy-2,4-dihydroxy-pyrimidine was prepared from ethoxymethylene malonic ester and urea. M.p. 241°–243°C. The following compounds were prepared in analogous manner:

a. 5-Carbethoxy-4-hydroxy-2-morpholino-pyrimidine from ethoxymethylene malonic ester and morpholino-guanidine. M.p. 164°–166°C (ethanol).

b. 5-Carbethoxy-4-hydroxy-2-thiomorpholino-pyrimidine from ethoxymethylene malonic ester and thiomorpholino-quanidine. M.p. 163°–165°C (ethanol).

EXAMPLE Y

5-Carbethoxy-2-chloro-4-thiomorpholino-pyrimidine 4 gm (0.018 mol) of 5-carbethoxy-2,4-dichloro-pyrimidine [prepared according to A. Dornow, G.

Petsch, Liebigs Ann. Chem. 588, 45 to 61 (1954)] were dissolved in 70 ml of ice-cold ethanol, and a solution of 4.1 gm (0.036 mol) of thiomorpholine was added at 0°C while stirring. The thick crystal slurry formed thereby was poured into 150 ml of water after stirring for 15 minutes. The resulting crystals were suction-filtered off and washed with water. M.p. 70°–71°C; yield: 4.8 gm (92.3% of theory).

Analysis: $C_{11}H_{14}ClN_3OS$; molecular weight 287.75. Calculated: C - 45.91%; H - 4.90%; N - 14.60%. Found: C - 46.10%; H - 5.06%; N - 14.66%.

The following compounds were prepared in analogous manner:

a. 5-Carbethoxy-2-chloro-4-(1,1-dioxido-thiomorpholino)pyrimidine from 5-carbethoxy-2,4-dichloro-pyrimidine and thiomorpholine-1,1-dioxide. M.p. 143°–147°C (petroleum ether/ethyl acetate).

b. 5-Carbethoxy-2-chloro-4-(1-oxido-thiomorpholino-pyrimidine from 5-carbethoxy-2,4-dichloro-pyrimidine and thiomorpholine-1-oxide. M.p. 123°–126°C (butanol/cyclohexane).

c. 5-Carbethoxy-2-chloro-4-(1,1-dioxido-thiomorpholino)-6-methyl-pyrimidine from 5-carbethoxy-2,4-dichloro-6-methyl-pyrimidine [prepared analogous to A. Dornow, G. Petsch, Liebigs Ann. Chem. 588, 45 to 61 (1954) from 5-carbethoxy-2,4-dihydroxy-6-methyl-pyrimidine, obtained according to method of R. W. Lamon, J. Het. Chem. 6, 261 to 264 (1969), and phosphorus oxychloride/phosphoric pentachloride] and thiomorpholine-1,1-dioxide. M.p. 145°–148°C.

EXAMPLE Z

5-Carbethoxy-4-chloro-2-morpholino-pyrimidine 14.4 gm (0.057 mol) of 5-carbethoxy-4-hydroxy-2-morpholino-pyrimidine were added to a mixture of 100 ml of phosphorus oxychloride and 7 gm of phosphorus pentachloride, and the mixture was refluxed for 20 minutes, whereby a clear solution was formed. The excess phosphorus oxychloride was distilled off, the residue was carefully decomposed with ice water, and the aqueous solution was made weakly alkaline by addition of sodium bicarbonate. The crystals formed thereby were suction-filtered off and recrystallized from ethanol. M.p. 79°–80.5°C.

5-Carbethoxy-4-chloro-2-thiomorpholino-pyrimidine was prepared in analogous manner from 5-carbethoxy-4-hydroxy-2-thiomorpholino-pyrimidine and phosphorus oxychloride/phosphoruc pentachloride. M.p. 81°–83°C (ethanol). Preparation of end products of the formula I:

EXAMPLE 1

6-Methyl-4-morpholino-5-nitro-2-piperazino-pyrimidine

A solution of 2.6 gm (0.01 mol) of 2-chloro-6-methyl-4-morpholino-5-nitro-pyrimidine (m.p. 127°–129°C, prepared from 2,4-dichloro-6-methyl-5-nitro-pyrimidine and morpholine) in 100 ml of acetone/dioxane (1:1) was added dropwise, while stirring and cooling, to a solution of 19.4 gm (0.1 mol) of piperazine hexahydrate in 300 ml of acetone/dioxane (1:1) at about 5°C. After about 1 hour the solvents were distilled off in vacuo, and the residue was taken up in about 100 ml of water. The insoluble reaction product was suction-filtered off, washed with water and dried. Yield: 3.0 gm (97% of theory). After one reprecipitation from about 0.2 N hydrochloric acid with 2 N ammonia, the reaction product of the formula

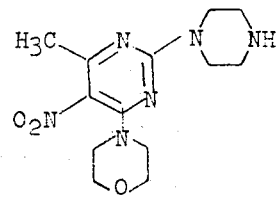

had a melting point of 143°–145°C.

Analysis: $C_{13}H_{20}N_6O_3$; molecular weight 308.3. Calculated: C - 50.65%; H - 6.55%; N - 27.21%. Found: C - 50.70%; H - 6.74%; N - 27.55%.

EXAMPLE 2

6-Methyl-5-nitro-2-piperazino-4-thiomorpholino-pyrimidine, m.p. 141°–143°C (ethyl acetate), was prepared analogous to Example 1 from 2-chloro-6-methyl-5-nitro-4-thiomorpholinopyrimidine (m.p. 106°–108°C) and piperazine.

EXAMPLE 3

6-Methyl-5-nitro-2-piperazino-4-(1-oxidothiomorpholino)pyrimidine, m.p. 176°–178°C (ethyl acetate), was prepared analogous to Example 1 from 2-chloro-6-methyl-5-nitro-4-(1-oxidothiomorpholino)-pyrimidine (m.p. 147°–150°C) and piperazine.

EXAMPLE 4

5-Nitro-2-piperazino-4-(1-oxido-thiomorpholino)-pyrimidine, m.p. 135°–145°C, was prepared analogous to Example 1 from 2-chloro-5-nitro-4-(1-oxido-thiomorpholino)-pyrimidine (m.p. 155°–157°C) and piperazine.

EXAMPLE 5

6-Ethyl-4-morpholino-5-nitro-2-piperazino-pyrimidine, m.p. 107°–109°C, was prepared analogous to Example 1 from 6-ethyl-2-chloro-4-morpholino-5-nitro-pyrimidine (m.p. 87°–88°C) and piperazine.

EXAMPLE 6

6-Ethyl-5-nitro-2-piperazino-4-thiomorpholino-pyrimidine, m.p. 111°–113°C, was prepared analogous to Example 1 from 6-ethyl-2-chloro-5-nitro-4-thiomorpholino-pyrimidine (m.p. 72°–73°C) and piperazine.

EXAMPLE 7

6-Ethyl-5-nitro-2-piperazino-4-(1-oxido-thiomorpholino)pyrimidine, m.p. 176°–178°C, was prepared analogous to Example 1 from 6-ethyl-2-chloro-5-nitro-4-(1-oxido-thiomorpholino)pyrimidine (m.p. 137°–138°C) and piperazine.

EXAMPLE 8

5-Nitro-2-piperazino-6-propyl-4-thiomorpholino-pyrimidine, m.p. 140°–142°C, was prepared analogous to Example 1 from 2-chloro-5-nitro-6-propyl-4-thiomorpholino-pyrimidine (resin) and piperazine.

EXAMPLE 9

5-Nitro-2-piperazino-6-propyl-4-(1-oxido-thiomorpholino)pyrimidine, m.p. 208°–210°C (methanol), was prepared analogous to Example 1 from 2-chloro-5- nitro-6-propyl-4-(1-oxido-thiomorpholino)-pyrimidine (m.p. 108°–111°C) and piperazine.

EXAMPLE 10

6-Isopropyl-5-nitro-2-piperazino-4-(1-oxido-thiomorpholino)pyrimidine, m.p. 175°–178°C (methanol), was prepared analogously to Example 1 from 2-chloro-6-isopropyl-5-nitro-4-(1-oxidothiomorpholino)-pyrimidine (m.p. 140°–142°C) and piperazine.

EXAMPLE 11

6-tert.Butyl-5-nitro-2-piperazino-4-(1-oxido-thiomorpholino)pyrimidine, m.p. 185°–188°C (methanol), was prepared analogous to Example 1 from 6-tert.butyl-2-chloro-5-nitro-4-(1-oxidothiomorpholino)-pyrimidine (m.p. 155°–157°C) and piperazine.

EXAMPLE 12

2-(N'-Carbethoxy-piperazino)-6-methyl-5-nitro-4-(1-oxidothiomorpholino)-pyrimidine, m.p. 150°–152°C (ethyl acetate), was prepared analogous to Example 1 from 2-chloro-6-methyl-5-nitro-4-(1-oxido-thiomorpholino)-pyrimidine (m.p. 147°–150°C) and N-carbethoxy-piperazine.

EXAMPLE 13

2-(N'-Formyl-piperazino)-6-methyl-5-nitro-4-(1-oxido-thiomorpholino)-pyrimidine, m.p. 202°–204°C (ethyl acetate), was prepared analogous to Example 1 from 2-chloro-6-methyl-5-nitro-4-(1-oxido-thiomorpholino)-pyrimidine (m.p. 147°–150°C) and N-formyl-piperazine.

EXAMPLE 14

4-(N'-Formyl-piperazino)-6-methyl-5-nitro-2-(1-oxido-thiomorpholino)-pyrimidine, m.p. 155°–158°C (water), was prepared analogous to Example 1 from 2-chloro-4-(N'-formyl-piperazino)-6-methyl-5-nitro-pyrimidine (m.p. 163°–165°C) and thiomorpholine-1-oxide.

EXAMPLE 15

6-Methyl-5-nitro-4-piperazino-2-(1-oxido-thiomorpholino)pyrimidine, m.p. 177°–180°C (water), was prepared from 4-(N'-formyl-piperazino)-6-methyl-5-nitro-2-(1-oxido-thiomorpholino)pyrimidine (m.p. 155°–158°C) by refluxing for some hours with sodium hydroxide in methanol.

EXAMPLE 16

5-Nitro-2-piperazino-4-(1-oxido-thiomorpholino)-6-pyrimidinecarboxylic acid methyl ester, m.p. 196°–198°C, decomp. (methanol), was prepared analogous to Example 1 from 2-chloro-5-nitro-4-(1-oxido-thiomorpholino)-6-pyrimidine-carboxylic acid methyl ester (m.p. 164°–165°C) and piperazine.

EXAMPLE 17

5-Nitro-2-piperazino-4-(1-oxido-thiomorpholino)-6-pyrimidinecarboxylic acid ethyl ester, m.p. 173°–175°C, was prepared analogous to Example 1 from 2-chloro-5-nitro-4-(1-oxido-thiomorpholino)-6-pyrimidine-carboxylic acid ethyl ester (m.p. 128°–130°C) and piperazine.

EXAMPLE 18

5-Chloro-6-cyano-2-piperazino-4-(1-oxido-thiomorpholino)pyrimidine 5.8 gm (0.02 mol) of 6-cyano-2,5-dichloro-4-(1-oxido-thiomorpholino)-pyrimidine (m.p. 145°–147°C), obtained from 6-cyano-2,4,5-trichloro-pyrimidine and thiomorpholine-1-oxide, were slowly added to a solution of 19.4 gm (0.1 mol) of piperazine hexahydrate in 100 ml of dioxane, whereby a mild endothermic reaction was released and a solution was rapidly formed. After standing for a short time, the reaction mixture was evaporated almost to dryness in vacuo, and the residue was taken up in about 100 ml of water. The reaction product, which separated out as pale yellow precipitate, was suction-filtered off, washed with water and dried. Yield: 6.4 gm (94% of theory); m.p. 203°–205°C.

After one reprecipitation from about 0.2 N hydrochloric acid with ammonia, the 5-chloro-6-cyano-2-piperazino-4-(1-oxido-thiomorpholino)-pyrimidine melted at 206°–208°C.

Analysis: $C_{13}H_{17}N_6OSCl$; molecular weight 340.8.
Calculated: C-45.81%; H-5.03%; S-9.41%; Cl-10.40%.
Found: C-45.50%; H-5.04%; S-9.45%; Cl-10.60%.

The same compound was also obtained from 5-chloro-6-cyano-2-piperazino-4-thiomorpholino-pyrimidine hydrochloride (m.p. 297°–299°C, decomp.), by oxidation with sodium metaperiodate in water.

EXAMPLE 19

5-Chloro-6-cyano-2-piperazino-4-thiomorpholino-pyrimidine, m.p. 137°–140°C, was prepared analogous to Example 18 from 6-cyano-2,5-dichloro-4-thiomorpholino-pyrimidine (m.p. 126°–127°C) and piperazine.

By recrystallization of the base from 0.1 N hydrochloric acid the hydrochloride, m.p. 297°–299°C (decomp.), was obtained.

EXAMPLE 20

5-Chloro-6-cyano-2-piperazino-4-(1,1-dioxido-thiomorpholino)pyrimidine 1.8 gm (0.005 mol) of 5-chloro-6-cyano-4-(1,1-dioxido-thiomorpholino)-2-ethylsulfonyl-pyrimidine (m.p. 234°–237°C, obtained from 2-ethylthio-5-chloro-6-cyano-4-thiomorpholino-pyrimidine by oxidation with potassium permanganate in dilute hydrochloric acid) were slowly added to a solution of 2.6 gm (0.03 mol) of piperazine in 50 ml of dioxane. After standing for a short time, the reaction solution was evaporated almost to dryness in vacuo, and the residue was taken up in about 50 ml of water. The insoluble reaction product was suction-filtered off, washed with water and dried. Yield: 1.4 gm (78% of theory).

After recrystallization from methanol/dioxane (9:1) the 5-chloro-6-cyano-2-piperazino-4-(1,1-dioxido-thiomorpholino)-pyrimidine melted at 235°–237°C.

Analysis: $C_{13}H_{17}N_6O_2SCl$; molecular weight 356.8.
Calculated: C-43.76%; H-4.80%; N-23.55%; Cl-9.94%.
Found: C-43.90%; H-4.83%; N-23.40%; Cl-10.00%.

The same compound was also obtained from 6-cyano-2,5-dichloro-4-(1,1-dioxido-thiomorpholino)-pyrimidine (m.p. 198°–199°C) by reaction with piperazine analogous to Example 18.

EXAMPLE 21

5-Chloro-6-cyano-2-piperazino-4-thiomorpholino-pyrimidine and its hydrochloride 1.0 gm (0.003 mol) of 5-chloro-6-cyano-2-phenoxy-4-thiomorpholino-pyrimidine (m.p. 112°–114°C, obtained from 6-cyano-2,5-dichloro-4-thiomorpholino-pyrimidine and sodium phenolate in phenol) was heated with 1.3 gm (0.015 mol) of piperazine in 50 ml of dioxane at about 50°C for 4 hours. After the major part of the solution thus obtained had been evaporated in vacuo, the residue was taken up in about 40 ml of water. The precipitated reaction product was suction-filtered off, washed with water and dried, yielding 0.7 gm (72% of theory) of the base.

After recrystallization of the base from 0.1 N hydrochloric acid, 5-chloro-6-cyano-2-piperazino-4-thiomorpholinopyrimidine hydrochloride, m.p. 297°–299°C (decomp.), was obtained.

Analysis: $C_{13}H_{17}N_6SCl \cdot HCl$; molecular weight 361.3. Calculated: N - 23.26%. Found: N - 23.62%.

The same base was obtained analogously from the 2-ethyl-thio-5-chloro-6-cyano-4-thiomorpholino-pyrimidine (m.p. 114°–117°C) by refluxing for about 8 hours with piperazine in dioxane.

EXAMPLE 22

5-Chloro-6-cyano-2-piperazino-4-(1-oxido-thiomorpholino)pyrimidine 0.3 gm (0.001 mol) of 5-chloro-6-cyano-4-phenoxy-2-piperazino-pyrimidine [m.p. 126°–128°C, obtained from 6-cyano-2,5-dichloro-4-phenoxy-pyrimidine and piperazine in acetone/dioxane (1:1) while cooling] were heated with 2.3 gm (0.02 mol) of thiomorpholine-1-oxide at about 140°C for 90 minutes. The dark colored molten mass was taken up in a small quantity of water, and the precipitated raw reaction product was purified on a silicagel column [eluant: methanol/concentrated ammonia (8:1)]. After reprecipitation from 0.2 N hydrochloric acid with ammonia, 5-chloro-6-cyano-2-piperazino-4-(1-oxido-thiomorpholino)-pyrimidine, m.p. 206°–208°C, was obtained.

EXAMPLE 23

5-Bromo-6-cyano-2-piperazino-4-thiomorpholino-pyrimidine was prepared analogous to Example 18 from 5-bromo-2-chloro-6-cyano-4-thiomorpholino-pyrimidine (m.p. 138°–142°C) and piperazine. By dissolving the base in acetone and adding ethanolic hydrochloric acid, the hydrochloride, m.p. 245°–247°C (decomp.), was obtained.

EXAMPLE 24

5-Bromo-6-cyano-2-piperazino-4-(1-oxido-thiomorpholino)-pyrimidine, m.p. 180°–185°C (acetone), was prepared analogous to Example 18 from 5-bromo-2-chloro-6-cyano-4-(1-oxido-thiomorpholino)-pyrimidine (m.p. 180°–182°C) and piperazine.

EXAMPLE 25

5-Chloro-2-piperazino-4-(1-oxido-thiomorpholino)-6-pyrimidine-carboxylic acid methyl ester, m.p. 160°–161°C, was prepared analogous to Example 18 from 2,5-dichloro-4-(1-oxido-thiomorpholino)-6-pyrimidine-carboxylic acid methyl ester (m.p. 140°–142°C) and piperazine.

EXAMPLE 26

5-Bromo-2-piperazino-4-(1-oxido-thiomorpholino)-6-pyrimidine-carboxylic acid methyl ester, m.p. 160°–163°C, was prepared analogous to Example 18 from 5-bromo-2-chloro-4-(1-oxido-thiomorpholino)-6-pyrimidine-carboxylic acid methyl ester (m.p. 166°–168°C) and piperazine.

EXAMPLE 27

5-Cyano-6-methyl-4piperazino-2-(1-oxido-thiomorpholino)-pyrimidine 2.7 gm (0.01 mol) of 4-chloro-5-cyano-6-methyl-2-(1-oxido-thiomorpholino)-pyrimidine (m.p. 251°–253°C, obtained from 5-cyano-2,4-dichloro-6-methyl-pyrimidine and thiomorpholine-1-oxide in acetone while cooling) were refluxed with a solution of 8.6 gm (0.1 mol) of piperazine in 80 ml of dioxane for about 30 minutes. The major part of the solvent was distilled off in vacuo, the residue was dissolved in about 80 ml of water, and a small quantity of 8 N sodium hydroxide was added, whereby the reaction product was first obtained as greasy, but soon solidifying precipitate. The product was suction-filtered off, washed with water and dried. Yield: 2.8 gm (87% of theory).

After one reprecipitation from about 0.2 N hydrochloric acid with 2 N sodium hydroxide and one recrystallization from water, 5-cyano-6-methyl-4-piperazino-2-(1-oxido-thiomorpholino)-pyrimidine, m.p. 215°–216°C, was obtained. Yield: 1.9 gm (59% of theory).

Analysis: $C_{14}H_{20}N_6OS$; molecular weight 320.4. Calculated: C-52.48%; H-6.29%; N-26.23%; S-10.01%. Found: C-52.10%; H-6.26%; N-26.05%; S-10.01%.

EXAMPLE 28

5-Chloro-6-methyl-2-piperazino-4-(1-oxido-thiomorpholino)-pyrimidine, m.p. 163°–165°C (ethyl acetate), was prepared analogous to Example 27 from 2,5-dichloro-6-methyl-4-(1-oxido-thiomorpholino)-pyrimidine (m.p. 125°–130°C) and piperazine.

EXAMPLE 29

5-Bromo-6-methyl-4-morpholino-2-piperazino-pyrimidine, m.p. 86°–90°C, was prepared analogous to Example 27 from 5-bromo-2-chloro-6-methyl-4-morpholino-pyrimidine (m.p. 98°–100°C) and piperazine.

EXAMPLE 30

5-Bromo-6-methyl-2-piperazino-4-thiomorpholino-pyrimidine, m.p. 111°–112°C, was prepared analogous to Example 27 from 5-bromo-2-chloro-6-methyl-4-thiomorpholino-pyrimidine (m.p. 125°–126°C) and piperazine.

EXAMPLE 31

5-Bromo-6-methyl-2-piperazino-4-(1-oxido-thiomorpholino)-pyrimidine, m.p. 158°–160°C, was prepared analogous to Example 27 from 5-bromo-2-chloro-6-methyl-4-(1-oxido-thiomorpholino)-pyrimidine (m.p. 128°–130°C) and piperazine.

EXAMPLE 32

5-Cyano-6-methyl-2-piperazino-4-thiomorpholino-pyrimidine 2.7 gm (0.01 mol) of 4-chloro-5-cyano-2-(N'-formyl-piperazino)-6-methyl-5-pyrimidine (m.p. 192°–194°C, obtained from 5-cyano-2,4-dichloro-6-methyl-pyrimidine and N-formylpiperazine in acetone while cooling) were refluxed with 2.1 gm (0.02. mol) of thiomorpholine in 60 ml of dioxane for about 1 hour. The solvent was distilled off in vacuo, and the residue was refluxed again in about 60 ml of isopropanol in the presence of sodium hydroxide for 30 minutes. After evaporation of the solvent in vacuo, the remaining raw reaction product was reprecipitated once from dilute hydrochloric acid with concentrated ammonia and recrystallized from methanol/water (1:1), yielding 1.6 gm (53% of theory) of 5-cyano-6-methyl-2-piperazino-4-thiomorpholino-pyrimidine, m.p. 146°–148°C.

Analysis: $C_{14}H_{20}N_6S$; molecular weight 304.4. Calculated: C-55.24%; H-6.62%; N-27.61%; S-10.54%. Found: C-55.35%; H-6.57%; N-27.43%; S-10.50%.

EXAMPLE 33

6-Methyl-5-nitro-2-piperazino-4-(1,1-dioxido-thiomorpholino)-pyrimidine

A solution of 0.8 gm (0.005 mol) of potassium permanganate in 30 ml of water was slowly added dropwise to a solution of 1.6 gm (0.005 mol) of 6-methyl-5-nitro-2-piperazino-4-thiomorpholino-pyrimidine (m.p. 141°–142°C) in about 60 ml of 0.5 N hydrochloric acid at about 5°C. After stirring the reaction mixture for 1 hour at about 5°C, the precipitated manganese dioxide was removed by means of a sodium bisulfite solution. The reaction product was precipitated by addition of concentrated ammonia, washed with water and dried (m.p. 208°–211°C). Yield: 1.4 gm (79% of theory).

After repeated reprecipitation of the raw product from 0.1 N hydrochloric acid with ammonia, 6-methyl-5-nitro-2-piperazino-4-(1,1-dioxido-thiomorpholino)-pyrimidine, m.p. 211°–213°C, was obtained.

Analysis: $C_{13}H_{20}N_6O_4S$; molecular weight 356.4. Calculated: C - 42.81%; H - 5.66%; S - 9.00%. Found: C - 43.60%; H - 5.74%; S - 9.06%.

EXAMPLE 34

5-Acetyl-2-piperazino-4-(1-oxido-thiomorpholino)-pyrimidine, m.p. 143°–145°C, was prepared analogous to Example 1 from 5-acetyl-2-chloro-4-(1-oxido-thiomorpholino)-pyrimidine (m.p. 168°–169°C, decomp.) and piperazine. For isolation, the raw product was taken up in water and the aqueous mixture was extracted with chloroform after a small quantity of the precipitated substance had been filtered off and sodium hydroxide solution had been added. The organic extract solution was dried, the chloroform was distilled off, and the residue was recrystallized once from ethyl acetate.

EXAMPLE 35

2-Formyl-piperazino-4-thiomorpholino-6-chloro-pyrimidine 125.1 gm of 4thiomorpholino-2,6-dichloro-pyrimidine (m.p. 118.5°–121.5°C) were dissolved in 1.2 liters of dioxane, a solution of 125.6 gm of N-formyl-piperazine in 0.1 liter of dioxane was added, and the mixture was refluxed for 2.5 hours. The precipitated N-formylpiperazine hydrochloride was suction-filtered off, and the filtrate was diluted with 2 liters of water and cooled in the ice bath. The precipitated white crystals were washed with a small quantity of 50% dioxane and dried at 100°C. Yield: 146 gm (90% of theory); m.p. 195°–198°C (decomp.).

EXAMPLE 36

2-Piperazino-4-thiomorpholino-5-nitro-6-cyclohexylamino-pyrimidine and its dihydrochloride 3.0 gm of 2-methylmercapto-4-thiomorpholino-5-nitro-6-cyclohexylamino-pyrimidine (m.p. 145°–146°C) were heated at 130°C with 8.0 gm of anhydrous piperazine for 1 hour in the molten state. Then, the mixture was diluted with 50 ml of water, whereupon a resinous product precipitated which slowly crystallized upon being triturated with acetone. The free base thus obtained was dissolved in acetone, the solution was filtered with activated charcoal, and ethereal hydrochloric acid was added to the filtrate, whereupon the dihydrochloride precipitated out. Yield: 2.6 gm (64.5% of theory); m.p. 173°C (decomp.).

EXAMPLE 37

2-(N'-Formyl-piperazino)-4-(1-oxido-thiomorpholino)-5-nitro-pyrimidyl-6-malonic acid diethyl ester 1.44 gm of sodium hydride were suspended in 20 ml of absolute dioxane, and, while stirring, a solution of 10.8 gm of malonic acid diethyl ester in 12 ml of dioxane was added dropwise, and then a hot solution of 5.84 gm of 2-(N'-formylpiperazino)-4-(1-oxido-thiomorpholino)-5-nitro-6-chloro-pyrimidine in 95 ml of dioxane was added. A red slurry of the sodium salt of 2-(formyl-piperazino)-4-(1-oxido-thiomorpholino)-5-nitro-pyrimidyl-6-malonic acid diethyl ester was immediately formed. The mixture was diluted with 100 ml of petroleum ether, and the precipitate was allowed to settle and was then suction-filtered off. The dried salt was taken up in 50 ml of water, and the solution was neutralized with 2 N hydrochloric acid and extracted with a mixture of chloroform and methanol (2:1). After evaporation of the combined extracts, a yellow, resinous product was obtained. Yield: 6.9 gm (88.0% of theory). The substance is pure in the thin-layer chromatogram (silicagel plate; eluant: benzene/ethanol/concentrated ammonia = 75:25:1); $R_f$-value = 0.55.

EXAMPLE 38

2-Piperazino-4-(1-oxido-thiomorpholino)-5-nitro-pyrimidyl-6-acetic acid ethyl ester 5.8 gm of sodium were dissolved in 100 ml of absolute ethanol, 4.35 gm of 2-(formyl-piperazino)-4-(1-oxido-thiomorpholino)-5-nitro-pyrimidyl-6-malonic acid diethyl ester (see preceding example) were added, and the resulting dark red solution was refluxed for 1.5 hours. Then, the ethanol was distilled off, the residue was taken up in ice-cold water, and the aqueous mixture was extracted with ethyl acetate. The extract was evaporated, leaving a resinous substance which was pure in the thin-layer chromatogram (silicagel plate; eluant: benzene/ethanol/concentrated ammonia = 75:25:1); $R_f$-value = 0.4; yield; 1.2 gm (34% of theory).

EXAMPLE 39

2-Piperazino-4-(1-oxido-thiomorpholino)-5-nitro-pyrimidyl-6-malonic acid diethyl ester hydrochloride 2.95 gm of 2-(formyl-piperazino)-4-(1-oxido-thiomorpholino)-5-nitro-pyrimidyl-6-malonic acid diethyl ester were dissolved in a mixture of 75 ml of ethanol and 75 ml of saturated ethanolic hydrochloric acid, and the solution was left standing for 24 hours at room temperature. Then, the solvent was distilled off in vacuo at room temperature, leaving a crystalline residue, which was recrystallized from ethanol.

Yield: 1.57 gm (52.3% of theory), m.p. above 335°C (decomp.). Thin-layer chromatogram: silicagel plate; eluant: benzene/ethanol/concentrated ammonia = 75:25:1; $R_f$-value = 0.25.

Analysis: $C_{19}H_{29}ClN_6SO_7$; molecular weight 521.00.
Calculated: C-43.80%; H-5.61%; N-16.13%; Cl-6.81%.
Found: C-43.80%; H-5.69%; N-15.87%; Cl-6.97%.

EXAMPLE 40

2-formyl-piperazino-4-(1-oxido-thiomorpholino)-5-nitro-6-(methyl-mercapto)-pyrimidine 0.27 gm of metallic sodium was dissolved in 15 ml of ethanol, and the solution was saturated with methyl mercaptan while at the same time nitrogen was passed through the reaction vessel as a protective gas. Then, a solution of 2-(formyl-piperazino)-4-(1-oxido-thiomorpholino)-5-nitro-6-chloro-pyrimidine in a mixture of 20 ml of ethanol and 20 ml of dioxane, heated to about 80°C, was poured in all at once. A precipitate of sodium chloride was obtained at once; for completion of the reaction, the mixture was stirred for another hour. Then, the solvents were distilled off, the residue was stirred with water, and the mixture was extracted three times with chloroform. After drying with sodium sulfate, the combined chloroform extracts were evaporated, and the viscous, yellow residue was recrystallized from ethyl acetate. Yield: 2.5 gm (62.5% of theory), m.p. 238°C.

EXAMPLE 41

2-Piperazino-4-(1-oxido-thiomorpholino)-5-nitro-6-methyl-mercapto-pyrimidine 1.8 gm of 2-(formyl-piperazino)-4-(1-oxido-thiomorpholino)-5-nitro-6-methylmercapto-pyrimidine (m.p. 168°-173°C) were heated with 50 ml of 2 N hydrochloric acid on a steam bath for 45 minutes. Then, the mixture was cooled to room temperature, anhydrous potassium carbonate was added until it was saturated, and the mixture was extracted with chloroform. After drying over potassium carbonate, the solvent was distilled off, and the residue was recrystallized from ethanol. Yield: 0.6 gm (36.1% of theory), m.p. 230°C.

EXAMPLE 42

2-(N'-Formyl-piperazino)-4-(1-oxido-thiomorpholino)-5-nitro-6-ethyl-mercapto-pyrimidine, was prepared analogous to Example 40 from 2-(N'-formyl-piperazino)-4-(1-oxido-thiomorphilino)-5-nitro-6-chloro-pyrimidine (m.p. 176°-178°C) and ethyl mercaptan. Yield: 63% of theory; m.p. 168°-173°C.

EXAMPLE 43

2-Piperazino-4-(1-oxido-thiomorpholino)-5-nitro-6-ethylmercapto-pyrimidine, was prepared analogous to Example 41 from 2-(N'-formyl-piperazino)-4-(1-oxido-thiomorpholino)-5-nitro-6-ethylmercapto-pyrimidine and 2 N hydrochloric acid. Yield: 67% of theory; m.p. 225°-228°C.

EXAMPLE 44

2-(N'-Formyl-piperazino)-4-(1-oxido-thiomorpholino)-5-nitro-6-mercapto-pyrimidine, was prepared analogous to Example 40 from 2-(N'-formyl-piperazino)-4-(1-oxido-thiomorpholino)-5-nitro-6-chloro-pyrimidine (m.p. 176°-178°C) and hydrogen sulfide. Yield: 87% of theory; m.p. above 240°C (decomp.).

EXAMPLE 45

2-(N'-Formyl-piperazino)-4-(1-oxido-thiomorpholino)-5-nitro-6-(n-propyl-mercapto)-pyrimidine 1.9 gm of 2-(N'-formyl-piperazino)-4-(1-oxido-thiomorpholino)-5-nitro-6-mercapto-pyrimidine [m.p. 240°C (decomp.)] were dissolved in 30 ml of methanol, and 0.7 gm of potassium methylate were added. Then, 1.2 gm of n-propyl bromide were added, and the mixture was stirred at room temperature for 5 hours. Then, the mixture was diluted with 100 ml of water, and the reaction product was extracted with chloroform. After drying with sodium sulfate, the extract solution was evaporated. A non-cyrstallizing, tough resin was obtained. Yield: 1.5 gm (71% of theory).

EXAMPLE 46

2-Piperazino-4-(1-oxido-thiomorpholino)-5-nitro-6-(n-propylmercapto)-pyrimidine, was prepared analogous to Example 41 from 2-(N'-formyl-piperazino)-4-(1-oxido-thiomorpholino)-5-nitro-6-(n-propyl-mercapto-pyrimidine and 2N hydrochloric acid. Yield: 62% of theory; m.p. 147°-150°C.

EXAMPLE 47

2-(N'-Formyl-piperazino)-4-(1-oxido-thiomorpholino)-5-nitro-6-(allyl-mercapto)-pyrimidine, was prepared analogous to Example 45 from 2-(N'-formyl-piperazino)-4-(1-oxido-thiomorpholino)-5-nitro-6-mercapto-pyrimidine and allyl bromide. A tough, non-crystallizing resin was obtained. Yield: 94% of theory.

EXAMPLE 48

2-Piperazino-4-(1-oxido-thiomorpholino)-5-nitro-6-(allyl-mercapto)-pyrimidine, was prepared analogous to Example 41 from 2-(N'-formyl-piperazino)-4-(1-oxido-thiomorpholino)-5-nitro-6-(allyl-mercapto)-pyrimidine and 2 N hydrochloric acid. Yield: 45% of theory; m.p. 139°C.

EXAMPLE 49

2-(N'-formyl-piperazino)-4-(1-oxido-thiomorpholino)-5-nitro-6-(cyclohexyl-amino)-pyrimidine 7.78 gm of 2-(N'-formyl-piperazino)-4-(1-oxido-thiomorpholino)-5-nitro-6-chloro-pyrimidine (m.p. 176°-178°C) were dissolved in 150 ml of dioxane, 4.35 gm of cyclohexylamine were added, and the mixture was refluxed for 1.5 hours. After cooling, the mixture was diluted with 200 ml of water and extracted three times with 50 ml of chloroform each. After drying the combined extracts with sodium sulfate, the solution was filtered with charcoal, the filtrate was evaporated, and the residue was recrystallized from 150 ml of ethanol. Yield: 7.6 gm (84.5% of theory); m.p. 254°-257°C.

EXAMPLE 50

2-Piperazino-4-(1-oxido-thiomorpholino)-5-nitro-6-cyclohexylamino-pyrimidine monohydrochloride 1.0 gm of 2-(N'-formyl-piperazino)-4-(1-oxido-thiomorpholino)-5-nitro-6-cyclohexylamino-pyrimidine (m.p. 254°-257°C) and 30 ml of 2 N hydrochloric acid were heated on the steam bath for 1.5 hours. Then, the mixture was filtered, and the filtrate was evaporated to dryness. The residue was recrystallized from ethanol. Yield: 0.7 gm (67% of theory); m.p. 273°–275°C (decomp.).

EXAMPLE 51

2-(N'-Formyl-piperazino)-4-(1-oxido-thiomorpholino)-5-nitro6-amino-pyrimidine, was prepared analogous to Example 49 from 2-(N'-formyl-piperazino)-4-(1-oxido-thiomorpholino)-5-nitro-6-chloro-pyrimidine (m.p. 176°–178°C) and concentrated ammonia in dioxane. Yield: 48.6% of theory; m.p. 256°–259°C.

EXAMPLE 52

2-(N'-Formyl-piperazino)-4-(1-oxido-thiomorpholino)-5-nitro-6-(methyl-amino)-pyrimidine, was prepared analogous to Example 49 from 2-(N'-formyl-piperazino)-4-(1-oxido-thiomorpholino)-5-nitro-6-chloro-pyrimidine (m.p. 176°–178°C) by reaction with methylamine in dioxane at room temperature for 20 hours. Yield: 54% of theory; m.p. 210°–214°C (decomp.).

EXAMPLE 53

2-Piperazino-4-(1-oxido-thiomorpholino)-5-nitro-6-methylamino-pyrimidine monohydrochloride, was prepared analogous to Example 50 from 2-(N'-formyl-piperazino)-4-(1-oxido-thiomorpholino)-5-nitro-6-methylamino-pyrimidine and 2 N hydrochloric acid. Yield: 76.5% of theory; m.p. 280°C (decomp.).

EXAMPLE 54

2-(N'-Formyl-piperazino)-4-(1-oxido-thiomorpholino)-5-nitro-6-(phenyl-amino)-pyrimidine, was prepared analogous to Example 49 from 2-(N'-formyl-piperazino)-4-(1-oxido-thiomorpholino)-5-nitro-6-chloro-pyrimidine (m.p. 176°–178°C) and aniline. Yield: 73.2% of theory; m.p. 200°–204°C.

EXAMPLE 55

2-Piperazino-4-(1-oxido-thiomorpholino)-5-nitro-6-(phenylamino)-pyrimidine, was prepared analogous to Example 41 from 2-(N'-formyl-piperazino)-4-(1-oxido-thiomorpholino)-5-nitro6-(phenyl-amino)-pyrimidine and 2 N hydrochloric acid. Yield: 46.4% of theory; m.p. 235°C.

EXAMPLE 56

2-(N'-Formyl-piperazino)-4-(1-oxido-thiomorpholino)-5-nitro-6-(p-chloro-phenyl-amino)-pyrimidine, was prepared analogous to Example 49 from 2-(N'-formyl-piperazino)-4-(1-oxido-thiomorpholino)-5-nitro-6-chloro-pyrimidine (m.p. 176°–178°C) and p-chloroaniline. Yield: 72.9% of theory; m.p. 248°C.

EXAMPLE 57

2-Piperazino-4-(1-oxido-thiomorpholino)-5-nitro-6-(p-chlorophenyl-amino)-pyrimidine monohydrochloride, was prepared analogous to Example 50 from 2-(N'-formyl-piperazino)-4-(1-oxido-thiomorpholino)-5-nitro-6-(p-chloro-phenyl-amino)pyrimidine and 2 N hydrochloric acid. Yield: 53.2% of theory; m.p. 300°C (decomp.).

EXAMPLE 58

2-(N'-Formyl-piperazino)-4-(1-oxido-thiomorpholino)-5-nitro-6-(o-carboxy-phenyl-amino)-pyrimidine, was prepared analogous to Example 49 from 2-(N'-formyl-piperazino)-4-(1-oxido-thiomorpholino)-5-nitro-6-chloro-pyrimidine (m.p. 176°–178°C) and anthranilic acid in the presence of three molar equivalents of triethylamine. Yield: 63% of theory; m.p. 163°–167°C (decomp.).

EXAMPLE 59

2-Piperazino-4-(1-oxido-thiomorpholino)-5-nitro-6-(o-carboxy-phenyl-amino)-pyrimidine monohydrochloride, was prepared analogous to Example 50 from 2-(N'-formyl-piperazino)-4-(1-oxido-thiomorpholino)-5-nitro-6-(o-carboxy-phenyl-amino)-pyrimidine and 2 N hydrochloric acid. Yield: 73.4% of theory; m.p. 290°C.

EXAMPLE 60

2-Piperazino-4-(1-oxido-thiomorpholino)-5-nitro-6-(o-carbo-methoxy-phenyl-amino)-pyrimidine dihydrochloride, was prepared analogous to Example 39 from 2-(N'-formyl-piperazino)-4-(1-oxido-thiomorpholino)-5-nitro-6-(o-carboxy-phenyl-amino)-pyrimidine and methanolic hydrochloric acid by refluxing for 3 hours. Yield: 53.5% of theory; m.p. 210°C (decomp.).

EXAMPLE 61

2-(N'-Formyl-piperazino)-4-(1-oxido-thiomorpholino)-5-nitro-6-(2-pyridyl-amino)-pyrimidine, was prepared analogous to Example 49 from 2-(N'-formyl-piperazino)-4-(1-oxido-thiomorpholino)-5-nitro-6-chloro-pyrimidine (m.p. 176°–178°C) and 2-amino-pyridine. Yield: 52% of theory; m.p. 240°–243°C.

EXAMPLE 62

2-Piperazino-4-(1-oxido-thiomorpholino)-5-nitro-6-(2-pyridyl-amino)-pyrimidine dihydrochloride, was prepared analogous to Example 39 from 2-(N'-formyl-piperazino)-4-(1-oxido-thiomorpholino)-5-nitro-6-(2-pyridyl-amino)-pyrimidine and methanolic hydrochloric acid. Yield: 73% of theory; m.p. 237.5°–240°C (decomp.).

EXAMPLE 63

2-(N'-Formyl-piperazino)-4-(1-oxido-thiomorpholino)-5-nitro-6-(4-pyridyl-amino)-pyrimidine, was prepared analogous to Example 49 from 2-(N'-formyl-piperazino)-4-(1-oxido-thiomorpholino)-5-nitro-6-chloro-pyrimidine and 4-amino-pyridine. Yield: 52.0% of theory; m.p. 240°–243°C.

EXAMPLE 64

2-Piperazino-4-(1-oxido-thiomorpholino)-5-nitro-6-(4-pyridyl-amino)-pyrimidine dihydrochloride, was prepared analogous to Example 39 from 2-(N'-formyl-piperazino)-4-(1-oxido-thiomorpholino)-5-nitro-6-(4-pyridyl-amino)-pyrimidine and methanolic hydrochloric acid. Yield: 81.8% of theory; m.p. 335°C (decomp.).

EXAMPLE 65

2-Piperazino-4-(1,1-dioxido-thiomorpholino)-5-nitro-6-cyclo-hexyl-amino-pyrimidine 68 gm of 2-piperazino-4-(1-oxido-thiomorpholino)-5-nitro-6-(cyclohexyl-amino)-pyrimidine were dissolved in 100 ml of 2 N sulfuric acid, the solution was cooled to 10°C, and over a period of 15 minutes a solution of 0.316 gm of potassium permanganate in 20 ml of 2 N sulfuric acid was added dropwise. The mixture was allowed to stand for 3 hours at 10°C, and then the precipitated brown crystals were suctionfiltered off; the filter cake was suspended in 30 ml of water, an excess of concentrated ammonia was added to the suspension, and the mixture was extracted with chloroform. The chloroform extract was evaporated, and the residue was recrystallized from ethanol. Yield: 0.25 gm (19% of theory); m.p. 214°–216°C.

EXAMPLE 66

5-Carbethoxy-4-(1,1-dioxido-thiomorpholino)-6-methyl-2-piperazino-pyrimidine 2.0 gm (0.006 mol) of 5-carbethoxy-2-chloro-4-(1,1-dioxido-thiomorpholino)-6-methyl-pyrimidine were added in small portions to a boiling solution of 5.2 gm (0.06 mol) of piperazine in 70 ml of dioxane, and the mixture was refluxed for 20 minutes. The reaction mixture was then poured into 150 ml of water, and the aqueous mixture was extracted with chloroform. The organic extract was washed with water, dried with sodium sulfate, and the solvent was removed in vacuo. The residue was recrystallized from ethanol/petroleum ether. Yield: 1.7 gm (74% of theory); m.p. 154°–159°C.

EXAMPLE 67

5-Carbethoxy-2-piperazino-4-(1-oxido-thiomorpholino)-pyrimidine, was prepared analogous to Example 66 from 5-carbethoxy-2-chloro-4-(1-oxido-thiomorpholino)-pyrimidine (m.p. 123°–126°C) and piperazine in dioxane (20 minutes, 100°C). Yield: 11% theory; m.p. of the base (monohydrate): 126°–130°C (decomp.; ethyl acetate/ether).

EXAMPLE 68

5-Carbethoxy-4-piperazino-2-thiomorpholino-pyrimidine, was prepared analogous to Example 66 from 5-carbethoxy-4-chloro-2-thiomorpholino-pyrimidine (m.p. 81°–83°C) and piperazine in dioxane (20 minutes, 100°C). Yield: 51% of theory; m.p. 94°–97°C (petroleum ether/ethyl acetate).

EXAMPLE 69

5-Carbethoxy-2-morpholino-4-piperazino-pyrimidine, was prepared analogous to Example 66 from 5-carbethoxy-4-chloro-2-morpholino-pyrimidine (m.p. 78°–80.5°C) and piperazine in dioxane (10 hours, 100°C). Yield: 33.4% of theory; m.p. 99°–101.5°C (petroleum ether/ethyl acetate).

EXAMPLE 70

5Carbethoxy-2-piperazino-4-(1,1-dioxido-thiomorpholino)pyrimidine, was prepared analogous to Example 66 from 2-chloro-5-carbethoxy-4-(1,1-dioxido-thiomorpholino)-pyrimidine (m.p. 143°–147°C) and piperazine in dioxane (2 hours, 100°C). Yield: 14.4% of theory; m.p. 160°–164°C (water).

EXAMPLE 71

5-Carbethoxy-2-piperazino-4-thiomorpholino-pyrimidine, was prepared analogous to Example 66 from 2-chloro-5-carbethoxy-4-thiomorpholino-pyrimidine (m.p. 70°–71°C) and piperazine in dioxane (2 hours, 100°C). Yield: 17.5% of theory; m.p. 115°C (petroleum ether/benzene).

EXAMPLE 72

2-Piperazino-4-(1-oxido-thiomorpholino)-5-fluoro-pyrimidine, was prepared analogous to Example 66 from 2-chloro-4-(1-oxido-thiomorpholino)-5-fluoro-pyrimidine (m.p. 179°–181°C) and piperazine by boiling for 2 hours in dioxane. Yield: 64% of theory; m.p. of the dihydrochloride semihydrate: 203°–205°C (ethanol/water).

EXAMPLE 73

6-Ethoxy-5-nitro-2-(1-oxido-thiomorpholino)-4-piperazino-pyrimidine, m.p. 108°–110°C (isopropanol/petroleum ether), was prepared from 6-ethoxy-5-nitro-4-piperazino-2-thiomorpholino-pyrimidine (m.p. 84°–86°C) and hydrogen peroxide (1 hour, 20°C).

EXAMPLE 74

6-Ethoxy-5-nitro-2-piperazino-4-thiomorpholino-pyrimidine 23 gm (0.07 mol) of 6-ethoxy-2-methylthio-5-nitro-4-thiomorpholino-pyrimidine were added to 68 gm (0.8 mol) of molten piperazine, and the mixture was heated at 110°C for 1 hour. After cooling, ice water was added to the reaction mixture, and the yellow precipitate formed thereby was suction-filtered off, washed with water and recrystallized from isopropanol. Yield: 18 gm (70% of theory); m.p. 166.5°–168.5°C Analysis: $C_{14}H_{22}N_6O_3S$; molecular weight 354.43. Calculated: C - 47.44%; H - 6.26%; S - 9.05%. Found: C - 47.50%; H - 6.23%; S - 9.02%.

EXAMPLE 75

6-Ethoxy-5-nitro-4-(1-oxido-thiomorpholino)-2-piperazino-pyrimidine, m.p. 223°–224°C (ethanol), was prepared analogous to Example 74 from 6-ethoxy-2-methylthio-5-nitro-4-(1-oxido-thiomorpholino)-pyrimidine and piperazine. (Reaction time: 20 minutes).

EXAMPLE 76

6-Allyloxy-5-nitro-2-piperazino-4thiomorpholino-pyrimidine, was prepared analogous to Example 74 from 6-allyloxy-2-methylthio-5-nitro-4-thiomorpholino-pyrimidine and piperazine (15 minutes, 120°C). M.p. of the base (semihydrate): 132°–133°C (carbon tetrachloride/petroleum ether).

EXAMPLE 77

6-Allyloxy-4-(1,1-dioxido-thiomorpholino)-5-nitro-2-piperazino-pyrimidine, m.p. 143°–147°C (isopropanol), was prepared analogous to Example 74 from 6-allyloxy-4-(1,1-dioxido-thiomorpholino)-2-methylthio-5-nitro-pyrimidine and piperazine (4minutes, 120°C).

EXAMPLE 78

6-(n-Propoxy)-4-(1,1-dioxido-thiomorpholino)-5-nitro-2-piperazino-pyrimidine, m.p. 166°–169°C (carbon tetrachloride), was prepared analogous to Example 74 from 6-(n-propoxy)-4-(1,1-dioxido-thiomorpholino)-2-methylthio-5-nitro-pyrimidine and piperazine (20 minutes, 120°C).

EXAMPLE 79

6-n-Propoxy-5-nitro-4-(1,1-oxido-thiomorpholino)-2-piperazino-pyrimidine, m.p. 170.5°–172.5°C (ethanol/water), was prepared analogous to Example 74 from 6-(n-propoxy)-2-methylthio-4-(1-oxido-thiomorpholino)-5-nitro-pyrimidine and piperazine (20 minutes, 120°C).

EXAMPLE 80

4-(1,1-Dioxido-thiomorpholino)-5-nitro-2-piperazino-6-isopropoxy-pyrimidine, m.p. 201°–202.5°C (ethanol), was prepared analogous to Example 74 from 4-(1, 1-dioxido-thiomorpholino)-2-methylthio-5-nitro-6-isopropoxy-pyrimidine and piperazine (20 minutes, 120°C).

EXAMPLE 81

6-n-Butoxy-5-nitro-4-(1-oxido-thiomorpholino)-2-piperazino-pyrimidine, was prepared analogous to Example 74 from 6-(n-butoxy)-2-methylthio-5-nitro-4-(1-oxido-thiomorpholino)-pyrimidine and piperazine (15 minutes, 130°C). M.p. of the hydrochloride: 160°–162°C (decomp.; from ether/acetone).

EXAMPLE 82

6-Neopentyloxy-5-nitro-2-piperazino-4-thiomorpholino-pyrimidine, m.p. 141.5°–143°C (ethyl acetate), was prepared analogous to Example 74 from 2-methylthio-6-neopentyloxy-5-nitro-4-thiomorpholino-pyrimidine and piperazine (30 minutes, 130°C).

EXAMPLE 83

5-Nitro-2-piperazino-6-isopropoxy-4-thiomorpholino-pyrimidine, m.p. 137.5°–140°C (isoproanol), was prepared analogous to Example 74 from 2-methylthio-5-nitro-6-isopropoxy-4-thiomorpholino-pyrimidine and piperazine (15 minutes, 130°C).

EXAMPLE 84

5-Nitro-4-(1-oxido-thiomorpholino)-2-piperazino-6-isopropoxy-pyrimidine, m.p. 204.5°–206°C (isopropanol), was prepared analogous to Example 74 from 2-methylthio-5-nitro-4-(1-oxido-thiomorpholino)-6-isopropoxy-pyrimidine and piperazine (15 minutes, 130°C).

EXAMPLE 85

6-(n-Butoxy)-4-(1,1-dioxido-thiomorpholino)-5-nitro-2-piperazino-pyrimidine, m.p. 181°–183°C (ethanol/water), was prepared analogous to Example 74 from 6-(n-butoxy)-4-(1,1-dioxido-thiomorpholino)-2-methylthio-5-nitro-pyrimidine and piperazine (15 minutes, 130°C).

EXAMPLE 86

6-(n-Butoxy)-5-nitro-2-piperazino-4-thiomorpholino-pyrimidine, m.p. 98°–100.5°C (ethanol/water), was prepared analogous to Example 74 from 6-(n-butoxy)-2-methylthio-5-nitro-4-thiomorpholino-pyrimidine and piperazine (15 minutes, 120°C).

EXAMPLE 87

6-(n-Butoxy)-4-morpholino-5-nitro-2-piperazino-pyrimidine, m.p. 63°–65°C (methanol/water), was prepared analogous to Example 74 from 6-(n-butoxy)-2-methylthio-4-morpholino-5-nitro-pyrimidine and piperazine (15 minutes, 120°C).

EXAMPLE 88

4-Morpholino-5-nitro-2-piperazino-6-isopropoxy-pyrimidine, m.p. 117°–119°C (isopropanol), was prepared analogous to Example 74 from 2-methylthio-4-morpholino-5-nitro-6-isopropoxy-pyrimidine and piperazine (10 minutes, 130°C).

EXAMPLE 89

6-(sec.Butoxy)-5-nitro-2-piperazino-4-thiomorpholino-pyrimidine, m.p. 123°–126°C (petroleum ether), was prepared analogous to Example 74 from 6-(sec.butoxy)-2-methylthio-5-nitro-4-thiomorpholino-pyrimidine and piperazine (20 minutes, 130°C).

EXAMPLE 90

6-(sec.Butoxy)-5-nitro-4-(1-oxido-thiomorpholino)-2-piperazino-pyrimidine, m.p. 156°–158°C (petroleum ether/carbon tetrachloride), was prepared analogous to Example 74 from 6-sec.butoxy)-2-methylthio-5-nitro-4-(1-oxido-thiomorpholino)-pyrimidine and piperazine (20 minutes, 130°C).

EXAMPLE 91

6-(sec.Butoxy)-4-(1,1-dioxido-thiomorpholino)-5-nitro-2-piperazino-pyrmidine, m.p. 163°–164.5°C (carbon tetrachloride), was prepared analogous to Example 74 from 6-(sec.butoxy)-4-(1,1-dioxido-thiomorpholino)-5-nitro-2-methylthio-pyrimidine and piperazine (20 minutes, 130°C).

EXAMPLE 92

6-Ethoxy-4-(1,1-dioxido-thiomorpholino)-5-nitro-2-piperazino-pyrimidine, was prepared analogous to Example 74 from 6-ethoxy-4-(1,1-dioxido-thiomorpholino)-2-methylthio-5-nitro-pyrimidine and piperazine (20 minutes, 120°C). M.p. of the base (semihydrate): 190°–193°C (carbon tetrachloride).

EXAMPLE 93

4-Morpholino-5-nitro-2-piperazino-6-(n-propoxy)-pyrimidine, m.p. 101°–104°C (petroleum ether), was prepared analogous to Example 74 from 2-methylthio-4-morpholino-5-nitro-6-(n-propoxy)-pyrimidine and piperazine (20 minutes, 120°C).

EXAMPLE 94

5-Nitro-2-piperazino-6-(n-propoxy)-4-thiomorpholino-pyrimidine, m.p. 92°–95°C (petroleum ether), was prepared analogous to Example 74 from 2-methylthio-5-nitro-6-(n-propoxy)-4-thiomorpholino-pyrimidine and piperazine (20 minutes, 120°C).

EXAMPLE 95

6-Ethoxy-5-cyano-4-(1,1-dioxido-thiomorpholino)-2-piperazino-pyrimidine, m.p. 235°C (ethanol), was prepared analogous to Example 74 from 6-ethoxy-5-cyano-2-methylthio-4-(1,1-dioxido-thiomorpholino)-pyrimidine (m.p. 194°C) and piperazine (30 minutes, 130°C).

EXAMPLE 96

6-Ethoxy-5-cyano-4-morpholino-2-piperazino-pyrimidine, was prepared analogous to Example 74 from 6-ethoxy-5-cyano-2-methylthio-4-morpholino-pyrimidine (m.p. 104°C) and piperazine (30 minutes, 120°C). M.p. of the hydrochloride: 239°C (ethanol).

EXAMPLE 97

6-Ethoxy-5-cyano-2-piperazino-4-thiomorpholino-pyrimidine, m.p. 119°C (petroleum ether), was prepared analogous to Example 74 from 6-ethoxy-5-cyano-2-methylthio-4-thiomorpholino-pyrimidine (m.p. 157°–159°C) and piperazine (30 minutes, 130°C).

EXAMPLE 98

5-Cyano-6-methoxy-4-(1-oxido-thiomorpholino)-2-piperazino-pyrimidine, m.p. decomposition >270°C (water), was prepared analogous to Example 74 from 5-cyano-6-methoxy-2-methylthio-4-(1-oxido-thiomorpholino)-pyrimidine (m.p. 184°–186°C) and piperazine (30 minutes, 130°C).

EXAMPLE 99

5-Cyano-4-(1-oxido-thiomorpholino)-2-piperazino-6-(n-propoxy)-pyrimidine, m.p. 177°–179°C (water), was prepared analogous to Example 74 from 5-cyano-2-methylthio-4-(1-oxido-thiomorpholino)-6-(n-propoxy)-pyrimidine (m.p. 190°–192°C) and piperazine (1.5 hours, 130°C).

EXAMPLE 100

5-Cyano-4-morpholino-2-piperazino-6-(n-propoxy)-pyrimidine, was prepared analogous to Example 74 from 5-cyano-2-methylthio-4-morpholino-6-(n-propoxy)-pyrimidine (m.p. 107°C) and piperazine (1.5 hours, 130°C). M.p. of the hydrochloride: decomposition >230°C.

EXAMPLE 101

5-Cyano-2-piperazino-6-(n-propoxy)-4-thiomorpholino-pyrimidine, was prepared analogous to Example 74 from 5-cyano-2-methylthio-6-(n-propoxy)-4-thiomorpholino-pyrimidine (m.p. 120°–122°C) and piperazine (1 hour, 130°C). M.p. of the hydrochloride: 248°C (ethanol).

EXAMPLE 102

6-Ethoxy-5-cyano-4-(1-oxido-thiomorpholino)-2-piperazino-pyrimidine, was prepared analogous to Example 74 from 6-ethoxy-5-cyano-2-methylthio-4-(1-oxido-thiomorpholino)-pyrimidine (m.p. 190°C) and piperazine (1 hour, 120C). M.p. of the base (semihydrate): 205°C (water).

EXAMPLE 103

6-Ethoxy-5-formyl-2-piperazino-4-thiomorpholino-pyrimidine, m.p. 110°–113°C (petroleum ether), was prepared analogous to Example 74 from 6-ethoxy-5-formyl-2-methylthio-4-thiomorpholino-pyrimidine (m.p. 101°C) and piperazine (1 hour, 130°C).

EXAMPLE 104

6-Ethoxy-5-formyl-4-(1-oxido-thiomorpholino)-2-piperazino-pyrimidine, m.p. 180°C (ethyl acetate), was prepared analogous to Example 74 from 6-ethoxy-5-formyl-2-methylthio-4-(1-oxido-thiomorpholino)-pyrimidine (m.p. 163°C) and piperazine (1 hour, 140°C).

EXAMPLE 105

6-Ethoxy-5-nitro-4-(1-oxido-thiomorpholino)-2-piperazino-pyrimidine 52 gm (0.6 mol) of piperazine were dissolved in 120 ml of boiling dioxane. 61.5 gm (0.18 mol) of 6-ethoxy-2-methylthio-5-nitro-4-(1-oxido-thiomorpholino)-pyrimidine were added over a period of 30 minutes to this solution. After refluxing for 45 minutes, the reaction mixture was poured into 1.5 liters of ice-water, and the yellow precipitate formed thereby was suction-filtered off, washed and recyrstallized from ethanol. Yield: 45.1 gm (65.8% of theory; m.p. 222°–223°C.

EXAMPLE 106

5-Cyano-6-methoxy-2-piperazino-4-thiomorpholino-pyrimidine, was prepared analogous to Example 105 from 5-cyano-6-methoxy-2-methylthio-4-thiomorpholino-pyrimidine (m.p. 134°C) and piperazine in dioxane (8 hours, 100°C). M.p. of the hydrochloride: 251°C (decomp.; from ethanol).

EXAMPLE 107

6-Ethoxy-5-nitro-4-(1-oxido-thiomorpholino)-2-piperazino-pyrimidine 50 gm (0.15 mol) of 6-ethoxy-2-methylthio-5-nitro-4-(1-oxido-thiomorpholino)-pyrimidine together with 64.8 gm (0.15 mol) of piperazine, were dissolved in 150 ml of dimethyl sulfoxide and the solution was stirred for 6 hours at room temperature. Then, the reaction mixture was poured into ice-water, the crystals formed thereby were suction-filtered off, and the filter cake was washed with water and recrystallized from ethanol. Yield: 39.3 gm (70.7% of theory); m.p. 222°–223°C.

By admixing an ethanolic solution of the base with an equivalent quantity of the corresponding acid, the following acid addition salts were obtained:

| | |
|---|---|
| Maleate: $C_{18}H_{26}N_6O_8S$ | M.p. 180–185°C (decomp.; from ethanal) |
| Fumarate: $C_{16}H_{26}N_6O_8S$ | M.p. 222–224°C (hydroscopic) |
| p-Toluenesulfonate: $C_{21}H_{30}N_6O_7S_2$ | M.p. 133–137°C (small quantity of methanol) |
| Succinate: $C_{16}H_{25}N_6O_6S$ | M.p. 194–196°C (decomp.; from methanol) |

EXAMPLE 108

6-Methoxy-5-nitro-4-(1-oxido-thiomorpholino)-2-piperazino-pyrimidine, m.p. 173°–175°C (isopropanol), was prepared analogous to Example 107 from 6-methoxy-2-methylthio-5-nitro-4-(1-oxido-thiomorpholino)-pyrimidine and piperazine in dimethylsulfoxide (4 hours, 20°C).

EXAMPLE 109

6-Ethoxy-5-nitro-4-(1-oxido-thiomorpholino)-2-piperazino-pyrimidine 12 gm (0.037 mol) of 6-ethoxy-2-chloro-5-nitro-4-(1-oxido-thiomorpholino)-pyrimidine were stirred together with 22 gm (0.28 mol) of piperazine in ethanol at 40°C for 2 hours. Then, the reaction mixture was poured into water, and the precipitate formed thereby was suction-filtered off and recrystallized from ethanol. Yield: 13 gm (93.8% of theory); m.p. 223°–224°C.

Analysis: $C_{14}H_{22}N_6O_4S$; molecular weight 370.4. Calculated: C - 45.39%; H - 5.99%; S - 8.66%. Found: C - 45.30%; H - 5.97%; S - 8.56%.

EXAMPLE 110

2,6-Di-(1-oxido-thiomorpholino)-4-morpholino-5-nitro-pyrimidine, m.p. 250°C, was prepared analogous to Example 109 from 2,6-dichloro-4-morpholino-5-nitro-pyrimidine (m.p. 129°–130°C) and thiomorpholino-1-oxide in ethanol (1 hour, 20°C).

EXAMPLE 111

6-Ethoxy-5-nitro-4-piperazino-2-thiomorpholino-pyrimidine, m.p. 84°–86°C (isopropanol/ethyl acetate), was prepared analogous to Example 109 from 6-ethoxy-4-chloro-5-nitro-2-thiomorpholino-pyrimidine and piperazine in ethanol (1 hour, 78°C).

EXAMPLE 112

5-Cyano-6-methoxy-4-piperazino-2-thiomorpholino-pyrimidine 18 gm (0.067 mol) of 4-chloro-5-cyano-6-methoxy-2-thiomorpholino-pyrimidine (m.p. 218°–219°C) were admixed with 60.3 gm (0.7 mol) of piperazine, and the mixture was heated at 130°C for 3 hours. After cooling, water was added, and the aqueous mixture was extracted with chloroform. The chloroform phase was dried, and the chloroform was removed in vacuo. The residue, the free base reaction product, was dissolved in hot ethanol, and the hydrochloride was precipitated by addition of ethanolic hydrochloric acid, suction-filtered off and washed with ethanol. Yield: 13 gm (54.8% of theory); m.p. 261°C.

Analysis: $C_{14}H_{21}ClN_6OS$; molecular weight 356.81. Calculated: C-47.18%; H-5.93%; N-23.52%; S-8.98%. Found: C-45.90% H-5.90%; N-23.55%; S-8.96%.

EXAMPLE 113

6-Ethoxy-5-nitro-2-piperazino-4-(1-oxido-thiomorpholino)-pyrimidine 2 gm (6 millimols) of 2,6-di-ethoxy-5-nitro-4-(1-oxido-thiomorpholino)-pyrimidine (m.p. 130°–132°C) were heated together with 8.6 gm (100 millimols) of piperazine at 125°C for 4 hours. The reaction mixture was then poured over ice, and the crystals formed thereby were suction-filtered off and recrystallized from ethanol. Yield: 0.53 gm (23.6% of theory); m.p. 221°–222°C.

EXAMPLE 114

6-Ethoxy-5-nitro-4-(1-oxido-thiomorpholino)-2-piperazino-pyrimidine 3.6 gm (0.01 mol) of 6-ethoxy-5-nitro-2-piperazino-4-thiomorpholino-pyrimidine were dissolved in 100 ml of methanol, a solution of 2.2 gm (0.01 mol) of sodium metaperiodate in 50 ml of water was added, and the mixture was refluxed for 4 hours. The reaction mixture was then poured into water, and the aqueous mixture was extracted with chloroform. The chloroform phase was dried, the chloroform was distilled off in vacuo, and the residue was recrystallized from ethanol. Yield: 2.9 gm (77% of theory); m.p. 223°–224°C.

EXAMPLE 115

6-Ethoxy-5-nitro-4-(1-oxido-thiomorpholino)-2-piperazino-pyrimidine 1 gm (2.9 mols) of 6-ethoxy-2-methylsulfinyl-5-nitro-4-(1-oxido-thiomorpholino)-pyrimidine [m.p. 164°–165°C, prepared from 6 ethoxy-2-methylthio-5-nitro-4-(1-oxido-thiomorpholino)-pyrimidine and 30% hydrogen peroxide in dilute acetic acid] was refluxed together with 5 gm (58 millimols) of piperazine in 50 ml of ethanol for 10 minutes. The reaction mixture was then poured into water, and the aqueous mixture was extracted with chloroform. The chloroform phase was dried, evaporated to dryness, and the residue was recrystallized from ethanol. Yield: 0.9 gm (84.7% of theory); m.p. 220°–222°C.

EXAMPLE 116

6-Ethoxy-5-nitro-4-(1-oxido-thiomorpholino)-2-piperazino-pyrimidine 1.2 gm (3 millimols) of 6-ethoxy-2-(N-formyl-piperazino)-5-nitro-4-(1-oxido-thiomorpholino)-pyrimidine (m.p. 209°–211°C) were refluxed together with 1.2 gm (30 millimols) of sodium hydroxide in 80 ml of methanol for 3 hours. The reaction mixture was then poured into water, and the aqueous mixture was extracted with chloroform. The chloroform phase was dried with sodium sulfate, and the chloroform was removed in vacuo. Yield: 1 gm (89.6% of theory), m.p. 222°–223°C (ethanol).

EXAMPLE 117

5-Cyano-6-methoxy-2-(1-oxido-thiomorpholino)-4-piperazino-pyrimidine and its hydrochloride A solution of 2.04 gm (0.01 mol) of 5-cyano-2,4-dichloro-6-methoxy-pyrimidine (m.p. 112°C) in 50 ml of dioxane was added to a solution of 2 gm of potassium carbonate in 10 ml of water, the mixed solution was cooled to 0°C, and a solution of 1.19 gm (0.01 mol) of thiomorpholine-1-oxide in 20 ml of dioxane was added dropwise while stirring and cooling. The 5-cyano-4-chloro-6-methoxy-2-(1-oxido-thiomorpholino)-pyrimidine which was now contained in the reaction mixture was right away further reacted in situ by addition of 4.3 gm (0.05 mol) of piperazine. After stirring the mixture for 3 hours at room temperature, water was added and the aqueous mixture was extracted with chloroform. The chloroform phase was dried with sodium sulfate, evaporated, and the residue was purified by column chromatography (silicagel for column chromatography, grainsize 0.2–0.5 mm; eluant: methanol/ammonia = 10:1). The uniform fractions were combined and evaporated to dryness. The residue, the free base reaction product, was taken up in ethanol, and the hydrochloride was precipitated by addition of ethanolic hydrochloric acid. Yield: 2.2 gm (59% of theory); m.p. decomposition > 243°C.

Analysis: $C_{14}H_{21}ClN_6O_2S$; molecular weight 372.89. Calculated: C - 45.09%; H - 5.67%; N - 22.53% Found: C - 44.85%; H - 5.57%; N - 22.45%.

EXAMPLE 118

5-Cyano-2-(1,1-dioxido-thiomorpholino)-6-methoxy-4-piperazino-pyrimidine, was prepared analogous to Example 117 from 5-cyano-2,4-dichloro-6-methoxy-pyrimidine (m.p. 112°C), thiomorpholine- 1,1-dioxide and piperazine. M.p. of the hydrochloride: 237°C (decomp.).

EXAMPLE 119

6-Neopentyloxy-5-nitro-4-(1-oxido-thiomorpholino)-2-piperazino-pyrimidine 4.5 gm (0.011 mol) of 6-neopentyloxy-5-nitro-2-piperazino-4-thiomorpholino-pyrimidine were suspended in a mixture of 60 ml of water and 11.4 ml (0.022 mol) of 2 N hydrochloric acid. 1.66 gm (0.011 mol) of 30% hydrogen peroxide were added to the suspension, and the mixture was stirred for 24 hours at room temperature, whereby a clear solution was obtained. The solution was made alkaline by careful addition of 12 ml of 2 N sodium hydroxide, and the yellow precipitate formed thereby was suction-filtered off, washed with water and recrystallized from a mixture of 30 ml of methanol and 20 ml of water. Yield: 2.4 gm (51.2% of theory); m.p. 156°–158°C.

Analysis: $C_{17}H_{28}N_6O_4S$; molecular weight 412.51.
Calculated: C-49.50%; H-6.87%; N-20.37%; S-7.77%
Found: C-49.30%; H-6.76%; N-20.43%; S-7.76%.

EXAMPLE 120

2,6-Di-ethoxy-5-nitro-4-(1-oxido-thiomorpholino)-pyrimidine 3.0 gm (9.3 millimols) of 6-chloro-2-methylthio-5-nitro-4-(1-oxido-thiomorpholino)-pyrimidine (m.p. 128°–131°C) were added at room temperature to a sodium ethylate solution prepared from 0.22 gm (9.4 millimols) of sodium and 30 ml of ethanol, and the mixture was refluxed for 2 hours. After standing for 20 hours at room temperature, the reaction mixture was poured into water, the aqueous mixture was extracted several times with chloroform/ethanol, the combined extract solutions were evaporated to dryness, and the residue was recrystallized from ethyl acetate/petroleum ether. Yield: 2 gm (65% of theory); m.p. 130°–132°C.

Analysis: $C_{12}H_{18}N_4O_5S$; molecular weight 330.35.
Calculated: C - 43.63%; H - 5.49%; N - 16.96%. Found: C - 43.70%; H - 5.38%; N - 16.80%.

EXAMPLE 121

2-(N'-Carbethoxy-piperazino)-6-methoxy-5-nitro-4-thiomorpholino-pyrimidine, m.p. 158°–159°C (methanol), was prepared analogous to Example 1 from 2-(N'-carbethoxy-piperazino)-6-chloro-5-nitro-4-thiomorpholino-pyrimidine (m.p. 134.5–136.5°C) and sodium methoxide in methanol in the presence of a small quantity of dimethylsulfoxide and potassium iodide (12 hours, 50°C).

EXAMPLE 122

6-Ethoxy-5-nitro-4-(1-oxido-thiomorpholino)-2-piperazino-pyrimidine 1 gm of 6-ethoxy-2-piperazino-4-thiomorpholino-pyrimidine was added to 3 ml of concentrated sulfuric acid, whereby the temperature of the resulting suspension rose to 50°C. After cooling to 0°C, 2 ml of concentrated nitric acid were added dropwise while stirring. After stirring it for another hour at room temperature, the reaction mixture was filtered through glass wool, and the filtrate was stirred into ice water. By careful addition of aqueous 40% sodium hydroxide, the mixture was adjusted to pH 9 and extracted with chloroform. The chloroform phase was washed with water, dried with sodium sulfate, and the solvent was distilled off in vacuo. The residue was recrystallized from ethanol. Yield: 0.8 gm (66.9% of theory); m.p. 223°–224°C.

EXAMPLE 123

2-(N'-Carboxypropionyl-piperazino)-6-methyl-5-nitro-4-(1-oxido-thiomorpholino)-pyrimidine A solution of 1.2 gm (0.012 mol) of succinic acid anhydride in 30 ml of acetone was slowly added, while stirring, to a solution of 3.4 gm (0.01 mol) of 6-methyl-5-nitro-4-(1-oxido-thiomorpholino)-2-piperazino-pyrimidine (m.p. 176°–178°C, obtained from 2-chloro-6-methyl-5-nitro-4-(1-oxido-thiomorpholino)-pyrimidine and piperazine in acetone-dioxane while cooling) in 200 ml of acetone. After standing for several hours, the precipitated crystalline reaction product was suction-filtered off, washed with a small quantity of ethanol/water (1:1) and dried. Yield: 3.7 gm (84% of theory).

After one recrystallization from ethanol/water (1:1), 2-(N'-carboxypropionyl-piperazino)-6-methyl-5-nitro-4-(1-oxido-thiomorpholino)-pyrimidine, m.p. 221°–223°C, was obtained.

EXAMPLE 124

2-(N'-Acetoacetyl-piperazino)-6-methyl-5-nitro-4-(1-oxido-thiomorpholino)-pyrimidine A solution of 0.9 gm (0.01 mol) of diketene in 10 ml of dioxane was slowly added, while stirring and cooling, to a suspension of 3.4 gm (0.01 mol) of 6-methyl-5-nitro-4-(1-oxido-thiomorpholino)-2-piperazino-pyrimidine in about 40 ml of dioxane. Subsequently, the resulting mixture was stirred for another hour at room temperature. The resulting clear solution was evaporated in vacuo, and the oily residue was digested with a small quantity of ethyl acetate, whereupon, after standing for some time, the oily product crystallized. The crystalline product was suction-filtered off, washed with a small quantity of methanol and dried. Yield: 3.9 gm (92% of theory).

After one recrystallization from methanol, 2-(N-acetoacetyl-piperazino)-6--methyl-5-nitro-4-(1-oxido-thiomorpholino)-pyrimidine, m.p. 174°–176°C, was obtained.

EXAMPLE 125

6-Methyl-2-(N'-nicotinoyl-piperazino)-5-nitro-4-(1-oxido-thiomorpholino)-pyrimidine A solution of 3.4 gm (0.01 mol) of 6-methyl-5-nitro-4-(1-oxido-thiomorpholino)-2-piperazino-pyrimidine in 50 ml of pyridine was slowly added at room temperature, while stirring, to a solution of 3.5 gm (0.02 mol) of nicotinic acid chloride hydrochloride in 60 ml of dry pyridine, and the resulting mixture was stirred for another hour. The major amount of the reaction solution was then evaporated in vacuo, and the residue was dissolved in a small quantity of water. The crystalline precipitate which formed after standing for some time was suction-filtered off and was immediately recrystallized once from ethanol. Yield: 3.4 gm (76% of theory) of 6-methyl-2-(N-nicotinoyl-piperazino)-5-nitro-4-(1-oxido-thiomorpholino)-pyrimidine, m.p. 145°–148°C.

EXAMPLE 126

2-(N'-Isonicotinoyl-piperazino)-6-methyl-5-nitro-4-(1-oxido-thiomorpholino)-pyrimidine, m.p.

208°–210°C, was prepared analogous to Example 125 from 6-methyl-5-nitro-4-(1-oxido-thiomorpholino)-2-piperazino-pyrimidine and isonicotinoyl chloride hydrochloride.

Example 127

6-Methyl-5-nitro-4-(1-oxido-thiomorpholino)-2-(N'-salicyloyl-piperazino)-pyrimidine, m.p. 143°–146°C, was prepared analogous to Example 125 from 6-methyl-5-nitro-4-(1-oxido-thiomorpholino)-2-piperazino-pyrimidine and salicyloyl chloride.

EXAMPLE 128

2-[N-(2-Furoyl)-piperazino]-6-methyl-5-nitro-4-(1-oxido-thiomorpholino)-pyrimidine, m.p. 189°–191°C, was prepared analogous to Example 125 from 6-methyl-5-nitro-4-(1-oxido-thiomorpholino)-2-piperazino-pyrimidine and furan-2-carbonyl chloride (dissolved in dioxane).

EXAMPLE 129

2-(N'-Methoxyacetyl-piperazino)-6-methyl-5-nitro-4-(1-oxido-thiomorpholino)-pyrimidine, m.p. 199°–202°C, was prepared analogous to Example 125 from 6-methyl-5-nitro-4-(1-oxido-thiomorpholino)-2-piperazino-pyrimidine and methoxyacetyl chloride (dissolved in dioxane).

EXAMPLE 130

2-(N'-Carbamoyl-piperazino)-4-(1-oxido-thiomorpholino)-5-nitro-6-(methyl-mercapto)-pyrimidine 1.9 gm of 2-piperazino-4-(1-oxido-thiomorpholino)-5-nitro-6-(methyl-metcapto)-pyrimidine (m.p. 230°C) were dissolved in a mixture of 5 ml of glacial acetic acid and 10 ml of water, and a solution of 2.0 gm of potassium cyanate in 25 ml of water was added dropwise at room temperature. About 10 minutes later, the raw product began to crystallize out. The product was recrystallized from ethanol. Yield: 1.3 gm (62.7% of theory); m.p. 264.0°C (decomp.).

EXAMPLE 131

2-(N'-Methylcarbamoyl-piperazino)-4-(1-oxido-thiomorpholino)-5-nitro-6-methyl-mercapto-pyrimidine 1.8 gm of 2-piperazino-4-(1-oxido-thiomorpholino)-5-nitro-6-(methyl-mercapto)-pyrimidine (m.p. 230°C) were suspended in 20 ml of dioxane, and a solution of 1 ml of methyl isocyanate was added dropwise over a period of 5 minutes. 10 minutes later, the reaction mixture was diluted with three times its volume of water, the aqueous mixture was extracted with a mixture of chloroform and ethanol (1:1), the extract was evaporated, and the residue was recrystallized from acetone. Yield: 2.02 gm (97.3% of theory); m.p. 265°C (decomp.).

EXAMPLE 132

2-(N'-Dimethylcarbamoyl-piperazino)-4-(1-oxido-thiomorpholino)-5-nitro-6-methyl-mercapto-pyrimidine 1.8 gm of 2-piperazino-4-(1-oxido-thiomorpholino)-5-nitro-6-(methyl-mercapto)-pyrimidine (m.p. 230°C) were suspended in dioxane containing 1.0 gm of triethylamine, 1.0 gm of dimethylcarbamoyl chloride was slowly added dropwise to the suspension, and the mixture was warmed to 50°C and then stirred for 30 minutes, whereby the reaction mixture turned green. The reaction mixture was then poured into three times its volume of water, the aqueous mixture was extracted with chloroform, the extract was evaporated, and the residue was recrystallized from acetone. Yield: 2.1 gm (98% of theory); m.p. 213°–220°C.

EXAMPLE 133

2-(N'-tert.Butylcarbamoyl-piperazino)-4-(1-oxido-thiomorpholino)-5-nitro-6-methyl-mercapto-pyrimidine was prepared by reacting 1.0 gm of 2-piperazino-4-(1-oxido-thiomorpholino)-5-nitro-6-(methyl-mercapto)-pyrimidine (m.p. 230°C) with 1.0 gm of tert.butyl-isocyanate analogous to Example 131. Yield: 1.20 gm (94.8% of theory); m.p. 261°C.

EXAMPLE 134

2-[N'-(Methoxymethyl-carbamoyl-piperazino]-4-(1-oxido-thiomorpholino)-5-nitro-6-methyl-mercapto-pyrimidine was prepared by reacting 1.8 gm of 2-piperazino-4-(1-oxido-thiomorpholino)-5-nitro-6-(methyl-mercapto)-pyrimidine (m.p. 230°C) with 0.8 ml of methoxy-isocyanate analogous to Example 131. Yield: 1.9 gm (86.0% of theory); m.p. 202°–210°C (decomp.).

EXAMPLE 135

2-(N'-Methylsulfonyl-piperazino)-4-(1-oxido-thiomorpholino)-5-nitro-6-methyl-mercapto-pyrimidine was prepared by reacting 1.8 gm of 2-piperazino-4-(1-oxido-thiomorpholino)-5-nitro-6-(methyl-mercapto)-pyrimidine (m.p. 230°C) with 1.0 gm of methane sulfochloride in the presence of 1 gm of triethylamine analogous to Example 125. Yield: 0.9 gm (40% of theory); m.p. 233°–237°C.

EXAMPLE 136

2-(N'-Carbethoxy-piperazino)-4-(1-oxido-thiomorpholino)-5-nitro-6-methyl-mercapto-pyrimidine 4.0 gm of 2-(N'-carbethoxy-piperazino)-4-(1-oxido-thiomorpholino)-5-nitro-6-chloro-pyrimidine (m.p. 176°–178°C) were dissolved in 10 ml of methanol, and the resulting solution was slowly added dropwise to a solution of 0.7 gm of potassium methoxide in 40 ml of methanol to which 1.5 ml of liquid methylmercaptan had been added. The mixture was stirred for 2 hours, then diluted with 100 ml of water, and the raw reaction product which separated out was extracted with chloroform. The organic extract was dried with sodium sulfate, evaporated, and the residue was recrystallized from acetone. Yield: 3.3 gm (69.1% of theory); m.p. 191°–196°C.

EXAMPLE 137

5-Carbethoxy-4-(N'-formyl-piperazino)-6-methyl-2-thiomorpholino-pyrimidine 4.55 gm (0.044 mol) of thiomorpholine and 0.5 gm of potassium iodide were added to a solution of 6.24 gm (0.02 mol) of 5-carbethoxy-2-chloro-4-(N'-formyl-piperazino)-6-methyl-pyrimidine in 25 ml of dimethylsulfoxide, and the mixture was allowed to stand for 3 days at room temperature. Then, water was added, and the reaction mixture was extracted with ethyl acetate. The residue remaining after drying and evaporating of the organic extract was recrystallized from cyclohexane/ethyl acetate (4:1). Yield: 5.8 gm (76.3% of theory); m.p. 118.5°–119.5°C.

EXAMPLE 138

4-(N'-Acetoacetyl-piperazino)-5-carbethoxy-2-thiomorpholino-pyrimidine, was prepared analogous to Example 137 from 5-carbethoxy-4-chloro-2-thiomorpholino-pyrimidine (m.p. 81°–83°C) and N-acetoacetyl-piperazine in dimethylsulfoxide (4 hours, 20°C). $R_f$-value: 0.65 (polygram-silicagel plate: ethyl acetate/ethanol = 95:5).

Analysis: $C_{19}H_{27}N_5O_4S$; molecular weight 421.52. Calculated: C-54.14%; H-6.46%; N-16.61%; S-7.61%. Found: C-54.27%; H-6.57%; N-16.64%; S-7.85%.

EXAMPLE 139

5-Carbethoxy-4-(N'-formyl-piperazino)-6-methyl-2-(1-oxido-thiomorpholino)-pyrimidine, was prepared analogous to Example 137 from 5-carbethoxy-2-chloro-6-methyl-4-(N'-formyl-piperazino)-pyrimidine (m.p. 107.5°–110°C) and thiomorpholino-1-oxido in dimethylsulfoxide. Yield: 68% of theory; m.p. 153.5°–155°C (from ethyl acetate).

EXAMPLE 140

5-Carbethoxy-6-methyl-2-piperazino-4-(1-oxido-thiomorpholino)-pyrimidine, was prepared analogous to Example 138 from 5-carbethoxy-2-chloro-6-methyl-4-(1-oxido-thiomorpholino)-pyrimidine (m.p. 124°–126°C) and piperazine in dimethylsulfoxide (30 minutes, 20°C). M.p. of the fumarate: 188°–190°C (decomposition; from ethanol/acetone).

EXAMPLE 141

5-Carbethoxy-6-methyl-2-piperazino-4-thiomorpholino-pyrimidine, was prepared analogous to Example 137 from 5-carbethoxy-2-chloro-6-methyl-4-thiomorpholino-pyrimidine (m.p. 64°–65°C) and piperazine in dimethylsulfoxide (1 hour, 20°C). Yield: 60.6% of theory; m.p. 92.5°–94°C (from cyclohexane).

EXAMPLE 142

5-Carbethoxy-6-methyl-4-piperazino-2-thiomorpholino-pyrimidine and its fumarate 3.6 gm of 5-carbethoxy-4-(N'-formyl-piperazino)-6-methyl-2-thiomorpholino-pyrimidine were mixed with 15 ml of aqueous 10% hydrochloric acid, and the mixture was allowed to stand for 3 days at room temperature. The reaction mixture was then carefully made alkaline and extracted with ethyl acetate. The residue (1.8 gm of the free base) remaining after washing, drying and evaporating of the organic extract was dissolved in a mixture of 30 ml of acetone and 20 ml of ethanol by heating, and 0.32 gm of fumaric acid was added. Upon cooling, the fumarate precipitated in pure form. Yield: 1.55 gm (39.9% of theory); m.p. 152°–155°C (decomp.).

Analysis: $C_{18}H_{27}N_5O_4S$; molecular weight 409.51. Calculated: C - 52.79%; H - 6.65%; S - 7.83%. Found: C - 52.80%; H - 6.92%; S - 7.71%.

EXAMPLE 143

5-Carbethoxy-6-methyl-4-piperazino-2-(1-oxido-thiomorpholino)-pyrimidine, was prepared analogous to Example 142 from 5-carbethoxy-4-(N-formyl-piperazino)-6-methyl-2-(1-oxido-thiomorpholino)-pyrimidine (m.p. 153.5°–155°C) and 10% hydrochloric acid. M.p. of the fumarate: 145°–147°C (decomposition).

EXAMPLE 144

2-(N'-Acetoacetyl-piperazino)-6-ethoxy-5-nitro-4-(1-oxido-thiomorpholino)-pyrimidine, was prepared analogous to Example 134 from 6-ethoxy-5-nitro-2-piperazino-4-(1-oxido-thiomorpholino)-pyrimidine (m.p. 223°–224°C) and diketene. Yield: 55% of theory; m.p. 191°–192°C (from ethanol).

EXAMPLE 145

N-[6-Ethoxy-5-nitro-4-(1-oxido-thiomorpholino)-pyrimidine-2-yl]-N'-(3-carboxy-propionyl)-piperazine 3.75 gm (0.01 mol) of 6-ethoxy-5-nitro-4-(1-oxido-thiomorpholino)-2-piperazino-pyrimidine (m.p. 223°–224°C) were refluxed together with 2.0 gm (0.02 mol) of freshly distilled succinic acid anhydride in 50 ml of dioxane for 1 hour. The reaction solution was then evaporated to dryness, and the solid residue was recrystallized from ethyl acetate/isopropanol. Yield: 2.0 gm (42.5% of theory); m.p. 198°–200°C.

Analysis: $C_{18}H_{26}N_6O_7S$; molecular weight 470.51. Calculated: C-45.95%; H-5.57%; N-17.86%; S-6.81%. Found: C-46.20%; H-5.73%; N-17.85%; S-6.79%.

EXAMPLE 146

2-(N'-Nicotinoyl-piperazino)-4-(1-oxido-thiomorpholino)-5-nitro-6-methyl-mercapto-pyrimidine 2.6 gm of 2-piperazino-4-(1-oxido-thiomorpholino)-5-nitro-6-(methyl-mercapto)-pyrimidine (m.p. 230°C) were suspended in 25 ml of dry pyridine, and 1.87 gm of nicotinic acid chloride-hydrochloride were added in small portions. The resulting mixture was stirred for 1 hour, the pyridine was then distilled off, the residue was stirred for 3 hours with 100 ml of water, the aqueous mixture was suction-filtered, and the filter cake was recrystallized from isopropanol. Yield: 1.25 gm (33.2% of theory); m.p. 148°–150°C (from isopropanol).

EXAMPLE 147

2-(N'-Isonicotinoyl-piperazino)-4-(1-oxido-thiomorpholino)-5-nitro-6-methylmercapto-pyrimidine, was prepared by reacting 2.6 gm of 2-piperazino-4-(1-oxido-thiomorpholino)-5-nitro-6-(methyl-mercapto)-pyrimidine (m.p. 230°C) with 2.50 gm of isonicotinic acid chloride hydrochloride analogous to Example 146. Yield: 17.5% of theory; m.p. 140°–142°C (from isopropanol).

EXAMPLE 148

2-(N'-Carboxyacryloyl-piperazino)-6-methyl-5-nitro-4-(1-oxido-thiomorpholino)-pyrimidine, m.p. sintering above 95°C, was prepared analogous to Example 123 from 2-piperazino-6-methyl-5-nitro-4-(1-oxido-thiomorpholino-pyrimidine and maleic acid anhydride.

Analysis: $C_{17}H_{22}N_6O_6S$; molecular weight 438.5. Calculated: C - 46.55%; H - 5.05%; S - 7.31%. Found: C - 46.50%; H - 5.32%; S - 7.26%.

The compounds of the present invention, that is, those embraced by formula I above and their non-toxic, pharmacologically acceptable acid addition salts, have useful pharmacodynamic properties; more particularly, they exhibit a very effective antithrombotic activity. Moreover, those compounds wherein $R_1$ and/or $R_2$ are N'-acylated-piperazino are effective antithrombotics without effects upon the blood pressure.

The antithrombotic activity of the compounds of this invention, that is, their ability to inhibit thrombocyte aggregation and adhesiveness, and their acute toxicities were ascertained by the following methods:

1. Determination of inhibiting effect upon platelet aggregation in human blood plasma by the method of Born and cross, J. Physiol. 170, 397 (1964):

The platelet aggregation was measured in the platelet-rich plasma of normal, healthy human donors. The rate of decline of the optical density of the platelet suspension was measured and recorded photometrically after the addition of adenosine diphosphate (ADP). From the angle of inclination of the density curve, the speed of aggregation was concluded. The optical density was taken as the point on the curve where most light was transmitted. The smallest possible doses of ADP were chosen, but enough to result in irreversible aggregation. The plasma was incubated at 37°C for 10 minutes with varying quantities of the test compound before ADP was added.

2. Determination of inhibiting effect on platelet adhesiveness in human blood by the so-called retention test according to Morris (E. Deutsch, E. Gerlach and K. Moser: 1. Internationales Symposium uber Stoffwechsel und Membranpermeabilitat von Erythrozyten and Thrombozyten, Vienna, 1969; Georg Thieme Verlag, Stuttgart, Germany).

To determine the inhibiting action of the test compound on thrombocyte aggregation, 1 ml of human blood was pipetted into each of a plurality of small test tubes, and the test compound was added to give a final concentration of $5 \times 10^{-5}$ mol/liter or $1 \times 10^{-5}$ mol/liter. The tubes were incubated for 10 minutes at 37°C. 1 gm of glass beads (for gas-chromatography) was added to half of the tubes. Then, the stoppered tubes were attached to a disc mounted for rotation about a horizontal axis and rotated for 1 minute. By this means good contact was obtained between the glass beads and the blood. The tubes were then left standing at room temperature for another hour, after which time a satisfactory sedimentation of erythrocytes had taken place. 0.01 ml of the supernatant plasma was removed, diluted 1:8000 with celloscope solution, and the platelet count was read in a celloscope. The percentage reduction of the stickiness due to the presence of the test compound, compared to the tubes containing no glass beads, was measured (average values of 4–6 tests).

3. Acute toxicity

The acute toxicity of the test compounds was determined in mice (observation time: 14 days). The $LD_{50}$ was calculated from the percentage of animals which died within the observation time after administration, i.v. or p.o., of varying doses [see J. Pharmacol. exper. Therap. 96, 99 (1949)].

The following table shows the results obtained for a number of illustrative, representative compounds of the formula I, where A = 6-Methyl-5-nitro-2-piperazino-4-(1-oxido-thiomorpholino)-pyrimidine, B = 6-Methyl-5-nitro-2-piperazino-4-thiomorpholino-pyrimidine, C = 5-Chloro-6-cyano-2-piperazino-4-(1-oxido-thiomorpholino)-pyrimidine, D = 6-Ethoxy-5-nitro-4-(1-oxido-thiomorpholino)-2-piperazino-pyrimidine, E = 5-Nitro-4-(1-oxido-thiomorpholino)-2-piperazino-6-isopropoxy-pyrimidine, F = 6-sec.Butoxy-4-(1,1-dioxido-thiomorpholino)-5-nitro-2-piperazino-pyrimidine, G = 6-Methylthio-5-nitro-4-(1-oxido-thiomorpholino)-2-(N'-formyl-piperazino)-pyrimidine and H = 6-Methyl-5-nitro-4-(1-oxido-thiomorpholino)-2-(N'-acetoacetyl-piperazino)-pyrimidine

| Compound | Morris test % inhibition (10 $\mu$ mols/ liter | Born and Cross test (ADP) $EC_{50}$ mol/ liter** | $LD_{50}$ mgm/kg | |
|---|---|---|---|---|
| | | | i.v. | p.o. |
| A | 92 | $1.2 \times 10^{-8}$ | 160 | 600 |
| B | 66 | $3 \times 10^{-6}$ | 70 | 620 |
| C | 92 | $1.3 \times 10^{-7}$ | 101 | 836 |
| D | 100 | $2.5 \times 10^{-8}$ | 150 | 600 |
| E | 69 | $2 \times 10^{-7}$ | 170 | 500 |
| F | 61 | $8.5 \times 10^{-7}$ | 150 | 1500 |
| G | 2 | $5 \times 10^{-5}$ | | >1000 |
| H | 11+ | $10^{-4}$ | | >1000 |

*Concentration: 30$\mu$ mols/liter
**Concentration which causes a 50% alteration of the "optical density".

For pharmaceutical purposes the compounds according to the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.16 to 8.4 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 149

Tablets

The tablet composition was compounded from the following ingredients:

| | | |
|---|---|---|
| 2-(N'-Acetoacetyl-piperazino)-6-methyl-5-nitro-4-(1-oxido-thiomorpholino)-pyrimidine | 20.0 | parts |
| Lactose | 29.0 | " |
| Potato starch | 45.0 | " |
| Polyvinylpyrrolidone | 5.0 | " |
| Magnesium stearate | 1.0 | " |
| Total | 100.0 | parts |

Preparation:

The pyrimidine compound was admixed with the lactose and the potato starch, the mixture was homogeneously moistened with ethanolic 20% solution of the polyvinylpyrrolidone, the moist mass was passed through a 1.5 mm-mesh screen, dried at 45°C and again passed through a 1.0 mm-mesh screen. The granulate thus obtained was admixed with the magnesium stearate, and the composition was compressed into 100 mgm-tablets. Each tablet contained 20 mgm of the pyrimidine compound and was an oral dosage unit composition with effective antithrombotic action.

EXAMPLE 150

Coated pills

The pill core composition was compounded from the following ingredients:

| | | |
|---|---:|---|
| 2-(N'-Acetoacetyl-piperazino)-6-methyl-5-nitro-4-(1-oxido-thiomorpholino)-pyrimidine | 20.0 | parts |
| Lactose | 37.0 | " |
| Corn starch | 16.0 | " |
| Polyvinylpyrrolidone | 6.0 | " |
| Magnesium stearate | 1.0 | " |
| Total | 80.0 | parts |

Preparation:

The ingredients were compounded in the same manner as in the preceding example, the composition was compressed into 80 mgm-pill cores, the cores were coated with a thin shell consisting essentially of a mixture of sugar and talcum, and the coated pills were polished with beeswax. Each coated pill contained 20 mgm of the pyrimidine compound and was an oral dosage unit composition with effective antithrombotic action.

EXAMPLE 151

Hypodermic solution

The solution was compounded from the following ingredients:

| | | |
|---|---:|---|
| 2-(N'-Acetoacetyl-piperazino)-6-methyl-5-nitro-4-(1-oxido-thiomorpholino)-pyrimidine | 20.0 | parts |
| Polyethyleneglycol 600 | 100.0 | " |
| Distilled water q.s.ad | 2000.0 | " by vol. |

Preparation:

A sufficient amount of distilled water was boiled to purge it of air and was then cooled in an atmosphere of nitrogen. The polyethyleneglycol and the pyrimidine compound were dissolved in the pre-treated distilled water while maintaining the nitrogen atmosphere, the solution was diluted to the indicated volume with more pre-treated distilled water, and the solution was filtered until free from suspended matter. The entire procedure was performed in diffused light. The filtrate was filled into brown 2 cc-ampules in an atmosphere of nitrogen, and the filled ampules were sterilized for 20 minutes at 120°C and then sealed. Each ampule contained 20 mgm of the pyrimidine compound and its contents were an injectable dosage unit composition with effective antithrombotic action.

EXAMPLE 152

Drop solution

The solution was compounded from the following ingredients:

| | | |
|---|---:|---|
| 2-(N'-Formyl-piperazino)-6-methylthio-5-nitro-4-(1-oxido-thiomorpholino)-pyrimidine | 20.0 | parts |
| Cane sugar | 350.0 | " |
| Sorbic acid | 1.0 | " |
| Essence of cocoa | 5.0 | " |
| Ethanol | 200.0 | parts by vol. |
| Polyethyleneglycol 600 | 100.0 | " |
| Distilled water q.s.ad | 1000.0 | " |

Preparation:

The sorbic acid was dissolved in the ethanol, the same volume of distilled water was added, and the pyrimidine compound was dissolved therein (solution 1).

The sugar was dissolved in the remaining amount of water (solution 2).

Solution 2, the polyethyleneglycol and the essence of cocoa were stirred into solution 1, the resulting solution was filtered, and the filtrate was filled into brown bottles.

The entire compounding and bottling procedure was carried out in an atmosphere of nitrogen, and the filled bottles have to be stored in a dark room.

1 ml (20 drops) of the solution contained 20 mgm of the pyrimidine compound and was an oral dosage unit composition with effective antithrombotic action.

Analogous results were obtained when any one of the other pyrimidine compounds embraced by formula I or a nontoxic acid addition salt thereof was substituted for the particular pyrimidine compound in Examples 149 through 152. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

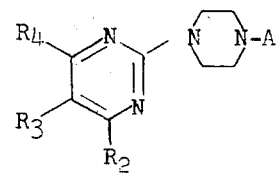

wherein
A is hydrogen, alkanoyl of 1 to 4 carbon atoms or acetyl-(alkanoyl of 1 to 4 carbon atoms),
$R_2$ is thiomorpholino, 1-oxido-thiomorpholino or 1,1-dioxido-thiomorpholino,
$R_3$ is chlorine, bromine or nitro, and
$R_4$ is cyano, alkyl of 1 to 3 carbon atoms, alkoxy of 1 to 6 carbon atoms or (alkyl of 1 to 6 carbon atoms)-mercapto,
or a non-toxic, pharmacologically acceptable acid addition salt thereof.

2. A compound of claim 1, which is 6-methyl-5-nitro-2-piperazino-4-(1-oxido-thiomorpholino)-pyrimidine or a non-toxic, pharmacologically acceptable acid addition salt thereof.

3. A compound of claim 1, which is 6-methyl-5-nitro-2-piperazino-4-thiomorpholino-pyrimidine or a nontoxic, pharmacologically acceptable acid addition salt thereof.

4. A compound of claim 1, which is 5-chloro-6-cyano-2-piperazino-4-(1-oxido-thiomorpholino)-pyrimidine or a non-toxic, pharmacologically acceptable acid addition salt thereof.

5. A compound of claim 1, which is 6-ethoxy-5-nitro-4-(1-oxido-thiomorpholino)-2-piperazino-pyrimidine or a non-toxic, pharmacologically acceptable acid addition salt thereof.

6. A compound of claim 1, which is 5-nitro-4-(1-oxido-thiomorpholino)-2-piperazino-6-isopropoxy-pyrimidine or a non-toxic, pharmacologically acceptable acid addition salt thereof.

7. A compound of claim 1, which is 6-sec.butoxy-4-(1,1-dioxido-thiomorpholino)-5-nitro-2-piperazino-pyrimidine or a non-toxic, pharmacologically acceptable acid addition salt thereof.

8. A compound of claim 1, which is 6-methylthio-5-nitro-4-(1-oxido-thiomorpholino)-2-(N'-formyl-piperazino)-pyrimidine or a non-toxic, pharmacologically acceptable acid addition salt thereof.

9. A compound of claim 1, which is 6-methyl-5-nitro-4-(1-oxido-thiomorpholino)-2-(N'-acetoacetyl-piperazino)-pyrimidine or a non-toxic, pharmacologically acceptable acid addition salt thereof.

* * * * *

PO-1050
(5/69)

UNITED STATES PATENT OFFICE
CERTIFICATE OF CORRECTION

Patent No. 3,975,384     Dated August 17, 1976

Inventor(s) BERTHOLD NARR, JOSEF ROCH, ERICH MÜLLER, WALTER HAARMANN

It is certified that error appears in the above-identified patent and that said Letters Patent are hereby corrected as shown below:

| | | |
|---|---|---|
| Col. 1, | line 48-49 | "fromyl" should read -- formyl -- |
| Col. 3, | line 36 | "aicd" should read -- acid -- |
| Col. 7, | line 10 | "20.4%" should read -- 29.4% -- |
| Col. 8, | line 37-38 | "methylthiol5-" should read -- methylthio-5- -- |
| Col. 8, | line 59 | "iospropoxy" should read -- isopropoxy -- |
| Col. 12, | line 62 | "quanidine" should read -- guanidine -- |
| Col. 25, | line 32 | After "11%" insert -- of -- |
| Col. 28, | line 27 | "pyrmidine" should read -- pyrimidine -- |
| Col. 31, | line 40 | "C-45.90%" should read -- C-46.90% -- |

Signed and Sealed this

Twenty-sixth Day of October 1976

[SEAL]

Attest:

RUTH C. MASON
Attesting Officer

C. MARSHALL DANN
Commissioner of Patents and Trademarks